(12) United States Patent
Boone et al.

(10) Patent No.: US 7,785,818 B2
(45) Date of Patent: *Aug. 31, 2010

(54) INFLAMMATORY BOWEL DISEASE AND IRRITABLE BOWEL SYNDROME IBD-FIRST CHEK DIAGNOSTIC PANEL

(75) Inventors: James Hunter Boone, Christiansburg, VA (US); David Maxwell Lyerly, Radford, VA (US); Tracy Dale Wilkins, Riner, VA (US)

(73) Assignee: Techlab, Inc., Blacksburg, VA (US)

( * ) Notice: Subject to any disclaimer, the term of this patent is extended or adjusted under 35 U.S.C. 154(b) by 799 days.

This patent is subject to a terminal disclaimer.

(21) Appl. No.: 10/693,377

(22) Filed: Oct. 24, 2003

(65) Prior Publication Data

US 2004/0137536 A1 Jul. 15, 2004

Related U.S. Application Data

(60) Provisional application No. 60/421,395, filed on Oct. 25, 2002.

(51) Int. Cl.
*G01N 33/53* (2006.01)
(52) U.S. Cl. ............... 435/7.24; 435/7.1; 435/7.92; 435/7.94; 436/518
(58) Field of Classification Search ............... None
See application file for complete search history.

(56) References Cited

U.S. PATENT DOCUMENTS 5,124,252 A * 6/1992 Guerrant et al. ............ 435/7.24
5,359,038 A 10/1994 Padron 5,455,160 A 10/1995 Fagerhol et al.

(Continued)

FOREIGN PATENT DOCUMENTS

EP 0615129 9/1994

(Continued)

OTHER PUBLICATIONS

Tabata et al, Nihon Rinsho Byori Gakkai, Dec. 1997, vol. 45(12, pp. 1201-1203, Measurement of fecal lactoferrin for diagnosis, English abstract.*

(Continued)

*Primary Examiner*—Robert B Mondesi
*Assistant Examiner*—Ginny Portner
(74) *Attorney, Agent, or Firm*—Shook, Hardy & Bacon L.L.P.

(57) ABSTRACT

A method for the differentiation of inflammatory bowel disease (IBD) from irritable bowel disease (IBS) followed by distinguishing ulcerative colitis and Crohn's disease from other gastrointestinal illnesses. This highly differential method first uses the presence of elevated lactoferrin as a marker of intestinal inflammation to differentiate IBD from IBS. Patients suspected of IBD are then analyzed for fecal anti-*Saccharomyces cerevisiae* antibodies (ASCA) as an indicator of Crohn's disease and fecal anti-neutrophil cytoplasmic antibodies (ANCA) as an indicator of ulcerative colitis. IBD patients are further monitored for intestinal inflammation using fecal lactoferrin to evaluate the effectiveness of medical therapy and to predict relapse. The apparatus comprises either a qualitative enzyme-linked immunoassay or other immunoassay that utilizes antibodies specific to human immunoglobins for the measurement of total endogenous lactoferrin, ASCA and ANCA in human feces. The method and apparatus can be used by healthcare providers to identify IBD and distinguish ulcerative colitis from Crohn's disease.

11 Claims, 2 Drawing Sheets

U.S. PATENT DOCUMENTS

| | | | |
|---|---|---|---|
| 5,552,292 | A * | 9/1996 | Uchida et al. ............ 435/7.23 |
| 5,681,699 | A | 10/1997 | Rotter et al. |
| 5,691,151 | A | 11/1997 | Braun |
| 5,750,355 | A * | 5/1998 | Targan et al. ............ 435/7.24 |
| 5,874,233 | A | 2/1999 | Targan et al. |
| 5,916,748 | A | 6/1999 | Targan et al. |
| 5,932,429 | A * | 8/1999 | Targan et al. ............ 435/7.24 |
| 5,935,574 | A * | 8/1999 | Broeker et al. ............ 424/141.1 |
| 5,968,741 | A | 10/1999 | Plevy et al. |
| 6,008,335 | A | 12/1999 | Rotter et al. |
| 6,074,835 | A | 6/2000 | Braun et al. |
| 6,174,664 | B1 | 1/2001 | Heine |
| 6,218,129 | B1 * | 4/2001 | Walsh et al. ............ 435/7.21 |
| 6,537,768 | B1 | 3/2003 | Braun |
| 6,562,629 | B1 | 5/2003 | Lin |
| 6,667,160 | B2 | 12/2003 | Fine |
| 6,727,073 | B1 * | 4/2004 | Moore et al. ............ 435/7.32 |
| 6,818,181 | B2 | 11/2004 | Lee |
| 6,872,540 | B2 * | 3/2005 | Boone et al. ............ 435/7.1 |
| 6,884,625 | B2 | 4/2005 | Lee |
| 7,192,724 | B2 * | 3/2007 | Boone et al. ............ 435/7.24 |
| 7,560,240 | B2 * | 7/2009 | Boone et al. ............ 435/7.1 |
| 2001/0036639 | A1 * | 11/2001 | Fine ............ 435/7.1 |
| 2002/0168698 | A1 * | 11/2002 | Boone et al. ............ 435/7.92 |
| 2002/0169286 | A1 | 11/2002 | Middeldorp et al. |
| 2003/0031625 | A1 * | 2/2003 | Lin et al. ............ 424/1.11 |
| 2003/0143649 | A1 * | 7/2003 | Boone et al. ............ 435/7.31 |
| 2004/0033537 | A1 * | 2/2004 | Boone et al. ............ 435/7.9 |
| 2004/0126898 | A1 * | 7/2004 | Boone et al. ............ 436/518 |
| 2004/0137536 | A1 * | 7/2004 | Boone et al. ............ 435/7.2 |
| 2005/0136495 | A1 * | 6/2005 | Boone et al. ............ 435/7.31 |
| 2006/0003392 | A1 * | 1/2006 | Oh et al. ............ 435/7.31 |
| 2008/0085524 | A1 * | 4/2008 | Lois ............ 435/7.24 |

FOREIGN PATENT DOCUMENTS

| | | | |
|---|---|---|---|
| WO | WO 92/16843 A1 | 10/1992 | |
| WO | 9739356 | 10/1997 | |
| WO | WO 97/39356 | 10/1997 | |
| WO | 9846997 | 10/1998 | |
| WO | WO 98/46997 | 10/1998 | |
| WO | 99/60403 | * 11/1999 | |
| WO | WO 99/60403 | 11/1999 | |
| WO | 0111334 | 2/2001 | |
| WO | WO 01/11334 A2 | 2/2001 | |
| WO | WO 01/36975 A1 | 5/2001 | |
| WO | 02/39883 | * 5/2002 | |
| WO | WO 02/39883 A2 | 5/2002 | |
| WO | 03036262 | * 5/2003 | |
| WO | 2004022713 | * 3/2004 | |
| WO | 2004037073 | * 5/2004 | |

OTHER PUBLICATIONS

Martins, Clovis A.P et al, Clinical and Diagnostic laboratory Immunology, Nov. 1995, vol. 2(6), pp. 763-765 Correlation of lactoferrin with Neutrophilic Inflammation in body fluids.*

Targan, Stephan R. et al, The Journal of Immunology, 1995, vol. 1565, pp. 3262-3267, Perinuclear anti-neutrophil cytoplasmic antibodies are spontaneously produced by mucosal B calls of Ulcerative Colitis Patients.*

Fine, Kenneth D et al, The American Journal of Gastroenterology, vol. 93(8), 1998, pp. 1300-1305, Utility of a Rapid Fecal latex agglutination Test Detecting the Neutrophil Protein, Lactoferrin, for Diagnosing Inflammatory Causes of Chronic Diarrhea.*

Nielsen, Ole H et al, The American Journal of Gastroenterology, vol. 95(2), 2000, pp. 359-367, Established and Emerging Biological Activity Markers of Inflammatory Bowel Disease.*

Bossuyt, Xavier, Clinical Chemistry, vol. 52(2), pp. 171-181, 2006, Serologic Markers in Inflammatory Bowel Disease.*

Peen et al, Gut, vol. 34, pp. 56-62,1993, Anti-lactoferrin antibodies and other types of ANCA in ulcerative colitis, primary sclerosing cholangitis and Crohn's disease.*

Tribble, JA et al, World J. Gastroenterology, 2001, vol. 7(4), p. 460-465, Non-invasive investigation of inflammatory bowel disease.*

Saitoh, O e tal, American Journal of GAStroenterology, Dec. 1999, vol. 94(12), pp. 3513-3520, Fecal eosinophil granule-derived proteins reflect disease activyt in inflammatory bowel disease.*

Kayazawa, Masanobut et al, The American Journal of Gastroenterology, vol. 97(2), Feb. 2002, pp. 360-369, Lactoferrin in Whole Gut Lavage Fluid as a Marker for Disease Activity in Inflammatory Bowel Disease: Copmarison with other neutrophil derived proteins.*

Hoffenberg, Edward J et al, Serologic testing for inflammatory bowel disease, pp. 447-452, Apr. 1999, Journal of Pediatrics, vol. 134.*

Quinton. JR e tal, Gut, 1998, vol. 42, pp. 788-791, Anti-*Saccharomyces cerevisiae* mannan antibodies combined with antineutrophil cytoplasmic autoantibodies in inflammatory bowel disease prevalence and diagnostic role.*

Ruemmele, Frank M. e tal, Gastroenterology, 1998, vol. 115, pp. 822-829, Diagnostic accuracy of serological assays in Pediatric inflammatory Bowel Disease.*

Koutroubakis, Ioannis E et al, The American Journal of Gastroenterology, vol. 96(2), 2001, pp. 449-454, Anti-*Saccharomyces cerevislae* Mannan Antibodies and Antineutrophil Cytoplasmic autoantibodies in Greek Patients with Inflammatory Bowel Disease.*

Nakamura, RM et al, MLO Med. Lab. Obs. Nov. 2001, vol. 33(11) pp. 8-15. quiz pp. 16,19.*

Bartunkova, J et al. Clinical Immunology, vol. 102(2) February, pp. 162-168, Antineutrophil Cytoplasmic antibodies. Anti-*Saccharomyces cervisiae* antibodies and Specific IgE to Food Allergens in Children with Inflammatory Bowel Diseases.*

Mamula, Peter, MD et al, The American Journal of Gastroenterology, vol. 97(8), pp. 2005-2010, Inflammatory Bowel Disease in Children 5 years of age and younger.*

Kossa, K et al, Eur. J. Gastroenterogyl. Hepatol, Aug. 1995, vol. 7(8), pp. 783-789, Anigen specificity of circulatting anti-neutrophil cytoplasmic antibodies in inflammatory bowel disease, (abstract only)p. 783.*

Sugi, Kazumori, MD et al, The American Journal of Gastroenterology, vol. 91(5), 1996, Fecal Lactoferrin as a Marker for Disease activity in Inflammatory Bowel Disease, Comparison with other neutrophil-derived proteins, pp. 927-934.*

Halme, L et al, Scand. J. Gastroenterol. Jun. 2002, vol. 37(6), pp. 692-698, Familal and sporadic inflammatory bowel disease: comparison of clinical features and serological markers in a genetically homogeneous population, (abstract only).*

Khan, K et al, Inflammatory Bowel Disease, pp. 325-329, vol. 8(5), 2002, Role of Serology and Routine Laboratory Tests in Childhood Inflammatory Bowel Disease.*

Taran et al (reference of record).*

Nielsen et al (reference of record).*

Fine et al, AJG, 1998, reference of record.*

R. Barnes, S. Allan, C. Taylor-Robinson, R. Finn, P. Johnson, "Serum Antibodies Reactive with *Saccharomyces cerevisiae* in Inflammatory Bowel Disease: Is IgA Antibody a Marker for Crohn's Disease?" *Int Arch Allergy Appl Immunol* (1990) 92, 9-15.

C. Faille, D. Mackenzie, J. Michalski, and D. Poulain, "Evaluation of an Enzyme Immunoassay Using Neoglycolipids Constructed from *Candida albicans* Oligomannosides to Define the Specificity of Anti-Mannan Antibodies" *Eur. J. Clin. Microbiol. Infect. Dis.*, (1992) May, 438-446.

M. Giaffer and C. Holdsworth, "Antibodies to *Saccharomyces cerevisiae* in patients with Crohn's disease and their possible pathogenic importance" *Gut* (1992) 33, 1071-1075.

S. Hanauer, "Inflammatory Bowel Disease" *The New England Journal of Medicine* (1996) 334, 841-848.

S. Hanauer and G. D'Haens, "Medical Management of Ulcerative Colitis" in Targan and Shanahan Inflammatory Bowel Disease: From Bench to Bedside, *Williams and Wilkens* (1994) 545-561.

C. Jongeneel, L. Briant, I. Udalova, A. Sevin, S. Nedospasov, and A. Thomsen, "Extensive genetic polymorphism in the human tumor necrosis factor region and relation to extended HLA haplotypes" *Proc. Natl. Acad. Sci. USA* (1991) 88, 9717-9721.

E. Lindberg, K. Magnusson, C. Tysk, and G. Jarnerot, "Antibody (IgG, IgA, and IgM) to baker's yeast *Saccharomyces cerevisiae*), yeast mannan, gliadin, ovalbumin and betalactoglobulin in monozygotic twins with inflammatory bowel disease" *Gut* (1991) 909-913.

J. Main, H. McKenzie, G. Yeaman, M. Kerr, D. Robson, C. Pennington, and D. Parratt, "Antibody to *Saccharomyces cerevisiae* (bakers' yeast) in Crohn's disease" *BMJ* (1988) 297 1105-1106.

H. McKenzie, J. Main, C. Pennington, and D. Parratt, "Antibody to selected strains of *Saccharomyces cerevisiae* (baker's and brewer's yeast) and *Candida albicans* in Crohn's disease" *Gut* (1990) 31, 536-538.

H. McKenzie, D. Parratt, J. Main, and C. Pennington, "Antigenic heterogeneity of strains of *Saccharomyces cerevisiae* and *Candida albicans* recognized by serum antibodies from patients with Crohn's disease" *FEMS Microbiology Immunology* (1992) 89, 219-224.

H. Yang, J. Rotter, H. Toyoda, C. Landers, D. Tyan, C. McElree, and S. Targan, "Ulcerative Colitis: A Genetically Heterogeneous Disorder Defined by Genetic (HLA Class II) and Subclinical (Antineutrophil Cytoplasmic Antibodies) Markers" *The American Society for Clinical Investigation, Inc.* (1993) 92, 1080-1084.

C. Young, A. Sonnenberg, and E. Bums, "Lymphocyte Proliferation Response to Baker's Yeast in Crohn's Disease" *Digestion* (1994) 55, 40-43.

M. Giaffer, A. Clark, C. Holdsworth, "Antibodies against *Saccharomyces cerevisiae* (Baker's & Brewer's yeast) in Crohn's Disease" *Gastorenterology* (1991) 100, No. 5, Part 2.

G. Barclay, H. McKenzie, J. Pennington, D. Parratt, and C. Pennington, "The Effect of Dietary Yeast on the Activity of Stable Chronic Crohn's Disease" *Scand J Gastroenterol* (1992) 27, 196-200.

M. Broker, H. Harthus, and R. Barnes, "A murine monoclonal antibody directed against a yeast cell wall glycoprotein antigen of the yeast genus *Saccharomyces*" FEMS Microbiology Letters (1994) 118, 297-304.

C. Darroch, S. Christmas, and R. Barnes, "In vitro human lymphocyte proliferative responses to a glycoprotein of the yeast *Saccharomyces cerevisiae*" *Immunology Letters* (1994) 81; 247-252.

B. Heelan, S. Allan, and R. Barnes, "Identification of a 200-kDa glycoprotein antigen of *Saccharomyces cerevisiae*" *Immunology Letters* (1991) 28, 181-186.

C. Galperin and M. Gershwin, Immunopathogenesis of Gastrointestinal and Hepatobiliary Diseases, *JAMA*, (1997) 278, 1946-1955.

R. Barnes, S. Allan, C. Robinson, R. Finn, and P. Johnson, "Serum Antibodies Reactive with *Saccharomyces cerevisiae* in Inflammatory Bowel Disease: Is IgA Antibody a Marker for Crohn's Disease?" *Int. Arch. Allergy Appl. Immuno* (1990) 92, 9-15.

J. Colombel, B. Sendid, J. Quinton, P. Jacquinot, O. Goulet, A. Cortot, D. Poulain, "Anti-*Saccharomyces cerevisiae* Antibodies: A New Subclinical Marker for Crohn's Disease" *Gastroenterology* (1996) 110, No. 4.

N. Oshitani, et al., *IgG subclasses of anti Saccharomyces cerevisiae antibody in inflammatory bowel disease*; Blackwell Science Ltd., European Journal of Clinical Investigation, vol. 31, pp. 221-225,2001.

Trulove SC, Witts LJ. Cortisone in Ulcerative Colities. Final Report on a Therapeutic Trial. British Medical Journal 1955; 4947:1041-1048.

Baveye, S., Elass, E., Mazurier, J., Spik, G., Legrand, D. Lactoferrine: a Multifunctional Glycoprotein Involved in the Modulation of the Inflammatory Response. Clin. Chem. Lab Med. 1999; 37(3):281-86.

Suleiman S, Sonnenberg A. Cost-effectiveness of Endoscopy in Irritable Bowel Syndrome. Arch Intern Med 2001; 161:369-75.

Levay, PF and Viljoen, J. Lactoferrin: a General Review. Haematologica. 1995; 80(3):256-67.

Roseth AG, Aadland E, Jahnsen J, Raknerud N. Assessment of Disease Activity in Ulcerative Colitis by Faecal Calprotectin, a Novel Granulocyte Marker Protein. Digestion 1997; 58:176-80.

Lagerholm S., Dutta SK, Merchant, NB, Nair, PP. COX-2 Expression in Fecal Colonocytes from Patients with Inflammatory Bowel Disease. Gastro 2001; 120:A16.

Hammer J., Talley NJ. Diagnosiic Criteria for the Irritable Bowel Syndrome. Am. J. Med. 1999; 107:5S-11S.

Limburg, P.L., Ahlquist, D.A., Sandborn, W., et al. Fecal Calprotectin Levels Predict Colorectal Inflammation among Patients with Chronic Diarrhea Referred for Colonoscopy. Amer. J. of Gastro. 2000; 95:2831-2837.

Steiner TS, Flores CA, Pizarro TT, Guerrant RL. Fecal Lactoferrin, Interleukin-1 Beta, and Interleukin-8 Are Elevated in Patients with Severe Clostridium Difficile Colitis. Clin Diagn Lab Immunol 1997; 4:719-22.

Naidu, A., Satyanarayan and Roland R. Arnold 1997. Influence of Lactoferrin on Host-Microbe Interactions. In T. William Hutchens and Bo Lonnerdal (ed.), Lactoferrin, pp. 259-275. Humana Press.

Andus T., Gross V., Caesar L, et al. PMN-elastase in Assessment of Patients with Inflammatory Bowel Disease. Dig. Dis. Sci. 1993; 35:97-105.

Tibble JA, Sigthorsson G, Bridger S. Fagerhol MK, Bjarnason I. Surrogate Markers of Intestinal Inflammation Are Predictive of Relapse in Patients with Inflammatory Bowel Disease. Gastroenterology 2000; 119:15-22.

Dwarakanath, AD, Finnie, IA, Beesley, C M, et al. Differential Excretion of Leukocyte Granule Components in Inflammatory Bowel Disease: Implications for Pathogenesis. Clin. Sci. 1997; 92:307-313.

Riley, L.W. 1995. Acute Inflammatory Diarrhea. In M. Blaser (ed.), P. Smith, J. Ravdin, H. Greenberg, and R. Guerrant, *Infections of the Gastrointestinal Tract*. Raven Press, New York, NY.

Tauxe, R., and M. Cohen. 1995. Epidemiology of Diarrhea Diseases in Developed Countries. In M. Blaser, P. Smith, J. Ravdin, H. Greenberg, and R. Guerrant (ed.), *Infections of the Gastrointestinal Tract*. Raven Press, New York, NY.

Sartor, R.B. 1995. Microbial Agents in Pathogenesis, Differential Diagnosis, and Complications of Inflammatory Bowel Disease. In M. Blaser, P. Smith, J. Ravdin, H. Greenberg, and R. Guerrant (ed.), *Infections of the Gastrointestinal Tract*. Raven Press, New York, NY.

Mathias, JR, Clench, MH, Reeves-Darby, VG, et al. Effect of Leuprolide Acetate in Patients with Moderate to Severe Functional Bowel Disease: Double-Blind, Placebo-Controlled Study. Dig Dis Sci, 1994; 39(6):1155-62.

Uchida, K., R. Matsuse, S. Tomita, K. Sugi, O. Saitoh, and S. Ohshiba. 1994. Immunochemical Detection of Human Lactoferrin in Feces as a New Marker for Inflammatory Gastrointestinal Disorders and Colon Cancer. Clin. Biochem. 27:259-264.

Sugi, K., Saitoh, O., Hirata, I., and K.. Katsu. 1996. Fecal Lactoferrin as a Marker for Disease Activity in Inflammatory Bowel Disease: Comparison with Other Neutophil-derived Proteins. Amer. J. Gastroenterol. 91:927-934.

Guerrant, R.L., V. Araujo, E. Soares, K. Kotloff, A. Lima, W. Cooper, and A. Lee. 1992. Measurement of Fecal Lactoferrin as a Marker of Fecal Leukocytes. J. Clin. Microbiol. 30:1238-1242.

Fine, K.D., F. Ogunji, J. George, M. Niehause, and R. Guerrant. 1998. Utility of a Rapid Fecal Latex Agglutination Test Detecting the Neutrophil Protein, Lactoferrin, for Diagnosing Inflammatory Causes of Chronic Diarrhea. Amer. J. Gastroenterol. 93:1300-1305.

Camilleri, M. 2001. Management of Irritable Bowel Syndrome. Gastroenterol. 120:652-668.

Calkins, Beverly M., Everhart, J.E. Ed 1994. Inflammatory Bowel Diseases, Digestive Diseases in the United States: Epidemiology and Impact., Chapter 16, pp. 509-550 U.S. Department of Health and Human Services, National Institute of Health, National Institute of Diabetes and Digestive and Kidney Diseases. U.S. Government Printing Office, NIH Publication No. 94-1447.

Sandler, Robert, Everhart, J.E. 1994. Irritable Bowel Syndrome, Digestive Diseases in the United States: Epidemiology and Impact., Chapter 19, pp. 596-612, U.S. Department of Health and Human Services, National Institute of Health, National Institute of Diabetes and Digestive and Kidney Diseases. U.S. Government Printing Office, NIH Publication No. 94-1447.

Harris, J.C., H.L. DuPont, and B.R. Hornick. 1971. Fecal Leukocytes in Diarrheal Illness. Ann. Intern. Med. 76:697-703.

Pool, et al. "Serum antineutrophil cytoplasmic autoantibodies in inflammatory bowel disease . . . " Gut, 1993, 46-50.

Peen, et al. "Distribution of lactoferrin and 60/65kDa heat shock protein in normal and inflamed human intestine and liver." Gut, 1996, 38, 135-140.

Peen, et al. Anti-lactoferrin antibodies and other types of ANCA in ulcerative colitis, primary sclerosing cholangitis, and Crohn's disease. Gut, 1993, 34, 56-62.

Vermeire, S. et al. Comparative Study of ASCA (Anti-*Saccharomyces cerevisiae* Antibody) Assays in Inflammatory Bowel Disease. Gastroenterolygy. 2001, vol. 120, pp. 827-833, see Materials and Methods all sections, and entire document.

Dubinsky, M.C. et al. Clinical Utility of Serodiagnoytic Testing in Suspected Pediatric Inflammatory Bowel Disease. American Journal of Gastroenterology (United States). Mar. 2001, vol. 96, No. 3, pp. 758-765, especially abstract "the combination of these serodiagnostic test could maximize diagnostic accuracy and minimize invasive investigations," and entire document.

Boone, J. H. et al. Measurement of Anti-*Saccharomyces cerevisiae* antibodies in human feces as an indicator of Crohn's disease. American Journal of Gastroenterology. Sep. 2002, vol. 97, No. 9, p. S253 (Abstract only).

Kazuo Uchida, et al., Immunochemical Detection of Human Lactoferrin in Feces as a New Marker for Inflammatory Gastrointestinal Disorders and Colon Cancer, Clinical Biochemistry, vol. 27, No. 4, pp. 259-264, 1994, The Canadian Society of Clinical Chemists.

Osamu Saitoh, M.D., et al., Fecal Eosinophil Granule-Derived Proteins Reflect Activity in Inflammatory Bowel Disease, The American Journal of Gastroenterology, vol. 94, No. 12, 1999.

Armitage & Colton, Random Sample, Encyclopedia of Biostatistics, John Wiley & Sons (1998), vol. 5, p. 3686.

Armitage & Colton, Sampling Distribution, Encyclopedia of Biostatistics, JohnWiley & Sons (1998), vol. 5, pp. 3933-3935.

Armitage & Colton, Sampling Frames, Encyclopedia of Biostatistics, John Wiley & Sons (1998), vol. 5, pp. 3935-3939.

Armitage & Colton, Selection Bias, Encyclopedia of Biostatistics, John Wiley & Sons (1998), vol. 5, p. 4045.

Darroch C J; Barnes R M R; Dawson J Journal of Clinical Pathology, 19990101 BMJ Publishing Group—ISSN 0021-9746 vol. 52, Nr:1, pp. 47-53.

Database Biosis [Online] Biosciences Information Service, Philadelphia, PA; 2002, Lecis Pierenrico, et al.: "[p-ANCA and ASCA Antibodies and the Differential Diagnosis Between Ulcerative Colitis and Crohn's Disease.]"; Recenti Progress in Medicina, vol. 93, No. 5, 2002.

Database CAPLUS on STN, AN 2003:463137. Kane et al. 'Fecal Lactoferrin is a sensitive and specific marker in identifying intestinal inflammation' American J. Gastroenterology, 2003, vol. 98, No. 6, p. 1309-1314. See Abstract, particularly the high specificity of the neutrophil marker in detecting patients.

Esaguy, N. et al. Mycobacteria and human autoimmune disease: direct evidence of cross-reactivity between human lactoferrin and the 65-kilodalton protein of tubercle and leprosy bacilli. Infection & Immunity. 1991;59:1117-1125.

Ferguson, A. et al. Technical report: results of immunological tests on faecal extracts are likely to be extremely misleading. CLiN. Exp. Immunol. 1995;99:70-75.

Functional Colonic Diseases, MeSH Database, National Library of Medicine & National Institutes of Health, available at http://www.ncbi.nlm.gov. 1 page total.

HCAPLUS Abstrcat of US 6667160 (one page).

Inflammatory Bowel Diseases, MeSH Database, National Library of Medicine & National Institutes of Health, available at http://www.ncbi.nlm.gov. 2 pages total.

Kapel N; et al European Journal of Clinical Chemistry and Clinical Biochemistry, 19920401 Walter De Gruyter, Berlin, DE—ISSN 0939-4974 vol. 30, pp. 197-202.

Kruzel et al. (Advances in Experimental Medicine and Biology, 1998, 443, pp. 167-173- Abstract Only). cited by examiner.

Mayet, W.J. et al. The pathophysiology of anti-neutrophil cytoplasmic antibodies (ANCA) and their clinical relevance. Crit. Rev. Oncol. Hematol. 1996;23:151-165.

Meillet D; et al Clinical and Experimental Immunology, 19870101 Wiley-Blackwell Publishing Ltd, GB—ISSN 0009-9104 vol. 69, pp. 142-147.

O'Mahony, S. et al. Appraisal of gut lavage in the study of intestinal humoral immunity. Gut. 1990;31 :1341-1344.

Picarelli, A. et al. Antiendomysial antibody detection in fecdal supernatants: In vivo proof that small bowel mucosa is the site of antiendomysial antibody production. Am. J. Gastroenterol. 2002;97:95-98.

Roozendaal, C., et al.: "Are Anti-Neutrophil Cytoplasmic Antibodies (ANCA) Clinically Useful in Inflammatory Bowel Disease (IBD)?" Clinical and Experimental Immunology, Oxford, GB, vol. 116, No. 2, May 1999.

Sanders, D.S. et al. Association of adult coeliac disease with irritable bowel syndrome: a case-control study in patients fulfilling ROME II criteria referred to secondary care. Lancet 2001 ;358: 1504-1508.

Sugi, K., Saitoh, O., Hirata, I., and K. Katsu. 1996. Fecal Lactoferrin as a Marker for Disease Activity in Inflammatory Bowel Disease: Comparison with Other Neutophil-derived Proteins. Amer. J. Gastroenterol. 91:927-934.

Tibble, J., Teahon, K., Thjodleifsson, B., et al., "A Simple Method for Assessing Intestinal Inflammation in Crohn's Disease" Gut 2000;47-506-513.

Tibble, J.A. and Bjarnason, I., "Non-Invasive Investigation of Inflammatory Bowel Disease" World J Gastroenterol, 2001;7(4):460-465.

U.S. Appl. No. 10/693,377, filed Oct. 24, 2003; USPTO Office Action Mailed: Sep. 5, 2006.

U.S. Appl. No. 10/693,377, filed Oct. 24, 2003; USPTO Office Action Mailed: Feb. 22, 2007.

U.S. Appl. No. 10/693,377, filed Oct. 24, 2003; USPTO Office Action Mailed: Sep. 25, 2007.

U.S. Appl. No. 10/693,377, filed Oct. 24, 2003; USPTO Office Action Mailed: Nov. 1, 2007.

USPTO Final Office Action mailed Jan. 26, 2007 for U.S. Appl. No. 10/656,034, filed Sep. 5, 2003.

USPTO Nonfinal Office Action mailed Aug. 9, 2006 for U.S. Appl. No. 10/656,034, filed Sep. 5, 2003.

USPTO Nonfinal Office Action mailed Jun. 3, 2009 for U.S. Appl. No. 10/656,034, filed Sep. 5, 2003.

USPTO Nonfinal Office Action mailed May 17, 2005 for U.S. Appl. No. 10/656,034, filed Sep. 5, 2003.

USPTO Nonfinal Office Action mailed Nov. 21, 2005 for U.S. Appl. No. 10/656,034, filed Sep. 5, 2003.

USPTO Nonfinal Office Action mailed Oct. 4, 2007 for U.S. Appl. No. 10/656,034, filed Sep. 5, 2003.

USPTO Office Action mailed Jan. 12, 2010 for U.S. Appl. No. 10/656,034, filed Sep. 5, 2003.

* cited by examiner

INFLAMMATORY BOWEL DISEASE AND IRRITABLE BOWEL SYNDROME IBD-FIRST CHEK DIAGNOSTIC PANEL

CROSS-REFERENCE TO RELATED APPLICATIONS

This application claims the benefit of U.S. Provisional Application No. 60/421,395, filed Oct. 25, 2002.

STATEMENT REGARDING FEDERALLY SPONSORED RESEARCH OR DEVELOPMENT

Not applicable.

TECHNICAL FIELD

A method for the differentiation of inflammatory bowel disease (IBD) from irritable bowel disease (IBS) followed by distinguishing ulcerative colitis from Crohn's disease and other gastrointestinal illnesses. This highly differential method first uses the presence of elevated fecal lactoferrin as a marker of intestinal inflammation to differentiate IBD from IBS. Patients suspected of IBD are then analyzed for anti-*Saccharomyces cerevisiae* antibodies (ASCA) as an indicator of Crohn's disease and fecal anti-neutrophil cytoplasmic antibodies (ANCA) as an indicator of ulcerative colitis. IBD patients are further monitored for intestinal inflammation using lactoferrin to evaluate the effectiveness of medical therapy and predict relapse. The apparatus comprises either a qualitative enzyme-linked immunoassay or other immunoassay that utilizes antibodies for the measurement of total endogenous lactoferrin, ASCA and ANCA in human feces. The method and apparatus can be used by healthcare providers to identify IBD and distinguish ulcerative colitis from Crohn's disease.

BACKGROUND OF THE INVENTION

An estimated 1 million Americans suffer from chronic inflammatory bowel disease (IBD) and 20 million Americans suffer from irritable bowel syndrome (IBS). IBD, comprised of both Crohn's Disease (CD) and ulcerative colitis (UC), is characterized by a chronic inflammatory response that results in histologic damage to the intestinal lining. Both CD and UC exhibit large numbers of leukocytes that migrate to the mucosa and into the intestinal lumen. Both diseases oscillate between active (i.e., presence of intestinal inflammation) and inactive (i.e., minimal to no intestinal inflammation) stages of disease activity. Active IBD can include symptoms such as bloody diarrhea, abdominal pain, and fever. The inactive stage has minimal to no intestinal inflammation and lacks severe gastrointestinal illness.

Patients who have active IBD but who exhibit mild signs and symptoms may be difficult to distinguish from patients with active IBS, an intestinal disorder of motility and the intestinal nervous system. Unlike IBD, IBS does not involve intestinal inflammation. In persons with IBS, the intestine appears normal upon endoscopic examination and leukocytes are not present in the mucosa or in fecal specimens. Symptoms can mimic those of IBD and include bloating, diarrhea, constipation, and severe and often debilitating abdominal pain. It is estimated that at least 20 million Americans suffer from IBS.

The similarity in symptoms between IBS and IBD renders rapid diagnosis difficult. However, given the potential severity of untreated IBD, differential diagnosis is crucial. The diagnosis of gastrointestinal illnesses, in general, is aided by diagnostic tests such as enzyme-linked immunosorbant assays (ELISAs), latex agglutination and lateral flow immunoassay. These tests are rapid and inexpensive methods for detecting markers in feces for enteric pathogens and inflammation. One marker of particular interest that has been found to be most specific for leukocytes in fecal specimens is lactoferrin. Human lactoferrin is an 80 kilodalton glycoprotein. This iron-binding protein is secreted by most mucosal membranes. It is a major component of the secondary granules found in polymorphonuclear neutrophils (PMNs), a primary component of the acute inflammatory response. Other hematopoietic cells such as monocytes and lymphocytes, do not contain lactoferrin, whereas various bodily secretions contain levels in the mg/mL range. During the process of inflammation, PMNs infiltrate the mucosa lining of the small and large intestine. This increase in the number of activated tissue leukocytes and exudation of plasma from ulcerated mucosa results in an increase in the level of lactoferrin found in feces. The protein is resistant to proteolysis and, as such, it provides a useful non-invasive fecal marker of intestinal inflammation.

Human lactoferrin has been used as a marker for fecal leukocytes in a number of applications. For instance, fecal lactoferrin has been used as a marker for leukocytes to distinguish noninflammatory diarrhea from inflammatory diarrhea, as disclosed in U.S. Pat. No. 5,124,252. Noninflammatory diarrhea caused by agents such as rotavirus, Norwalk-like agents and cholera, typically causes minimal to no intestinal damage and patients respond readily to oral rehydration. Inflammatory diarrheas include those caused by enteric pathogens such as *Clostridium difficile, Shigella* species, *Salmonella* species, *Campylobacter jejuni* and *Entamoeba histolytica* and those that have no clearly defined infectious agent such as CD and UC. U.S. Pat. No. 5,124,252 discloses an in vitro test for fecal leukocytes that aids in distinguishing inflammatory from noninflammatory diarrhea. The '252 patent discloses testing fecal samples suspected of containing leukocytes with an assay that utilizes an antibody for lactoferrin to determine the presence of leukocytes in the fecal sample.

Human lactoferrin also has been used as a marker for diagnosis of inflammatory gastrointestinal disorders, colon polyp and colorectal cancer as disclosed in U.S. Pat. No. 5,552,292. However, neither the method of the '252 patent nor that of the '292 patent disclose utility in distinguishing IBS from IBD. The samples tested by the assay of the '252 patent are samples suspected of containing leukocytes. This suspicion is owed to the patient presenting with diarrhea. However, 25-50% of persons having IBD do not present with diarrhea and, thus, the '252 patent does not relate to diagnosing etiology in such patients. As for the '292 patent, the disclosed method utilizes a 1:100 sample dilution which does not allow for accurate quantitation of lactoferrin levels. Further, the '292 patent discloses using partial forms of molecules for testing and not total endogenous lactoferrin, again affecting the accuracy of the quantitation. The method of the '292 patent also does not relate to utilizing lactoferrin levels to distinguish IBD from IBS. The population tested in the '292 patent, while including persons with UC and CD, did not include persons having IBS.

IBD is comprised of both Crohn's disease and ulcerative colitis. These two distinct diseases require a rapid differential diagnosis for optimal treatment. Crohn's disease may involve the entire gastrointestinal tract and include inflammation extending into the transmural mucosa, whereas ulcerative colitis affects solely the large bowel and includes inflammation of the innermost lining. Conventional methods to differentiate between Crohn's disease and ulcerative colitis utilizing multiple endoscopy examinations and histological analysis may take years to confirm a diagnosis.

U.S. Pat. No. 6,218,120 discloses a method of determining the presence of serum ANCA as a marker to diagnose IBD. However, it does not disclose a method for diagnosing ulcerative colitis in a patient diagnosed with IBD.

Serological methods for the differential diagnosis of CD and UC also are known in the art. For example, it is known to use the presence of serum anti-*Saccharomyces cerevisiae* antibodies (ASCA) to diagnose CD. See Main et al., Antibody to *Saccharomyces cerevisiae* (baker's yeast) in Crohn's disease, BMJ Vol. 297 (Oct. 29, 1988); Broker et al., A Murine Monoclonal Antibody Directed Against a Yeast Cell Wall Glycoprotein Antigen of the Yeast Genus *Saccharomyces*, FEMS Microbiology Letters 118 (1994), 297-304. It is further known in the art to use the presence of serum ASCA to diagnose clinical subtypes of UC and CD in patients presenting with established diagnoses. For example, U.S. Pat. No. 5,968,741 discloses utilizing the presence of serum ASCA to diagnose a medically resistant clinical subtype of UC in patients presenting with an established diagnosis of UC. Similarly, U.S. Pat. No. 5,932,429 discloses utilizing the presence of serum ASCA to diagnose a clinical subtype of CD in patients presenting with an established diagnosis of CD.

DETAILED DESCRIPTION OF THE INVENTION

Figure 1:
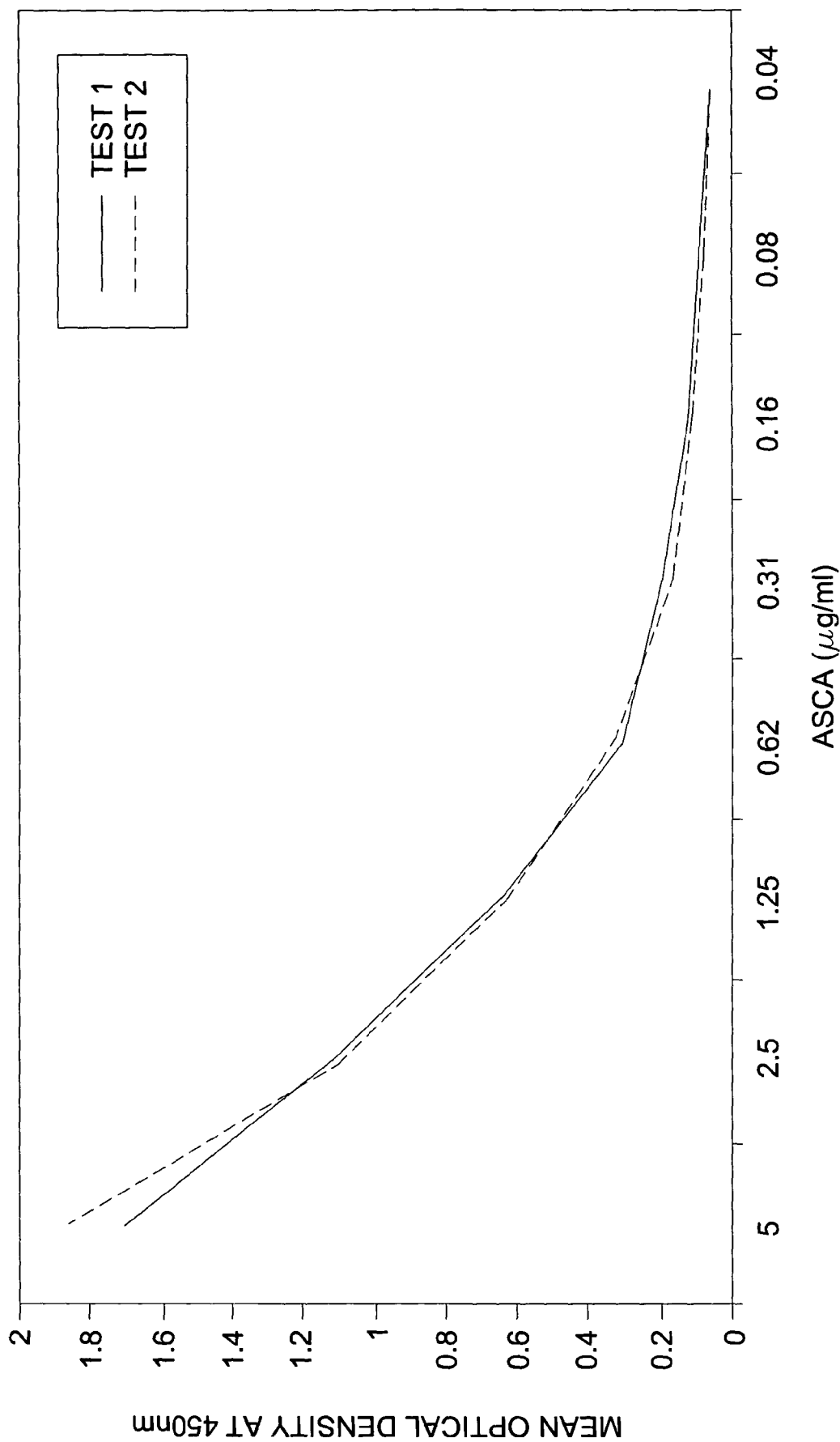
FIG. 1 is a graphical representation of a standard curve of purified anti-*Saccharomyces cerevisiae* antibodies in accordance with an embodiment of the present invention.

The present invention relates a lactoferrin immunoassay used to determine the presence of elevated lactoferrin as an indicator of intestinal inflammation thus aiding in the differentiation of IBD from IBS, and ANCA and ASCA immunoassays to differentiate between ulcerative colitis and Crohn's disease. The test results may be used to determine appropriate treatment for ulcerative colitis and Crohn's disease patients. Qualitative immunoassays such as enzyme-linked immunoassays and lateral flow dipsticks that utilize monoclonal and polyclonal antibodies to human ANCA and ASCA may be used distinguish between ulcerative colitis and Crohn's disease. Bodily secretions, as used herein may include, but are not limited to, feces and mucosal secretions, whole blood, serum, plasma, saliva or other bodily fluid or tissue.

In the qualitative assay, the bodily secretions are diluted and added to a well containing the immobilized antibodies to lactoferrin or antigens of *Saccharomyces cerevisiae* or neutrophil cytoplasmic antigens. If endogenous lactoferrin or ASCA or ANCA is present, it will bind to the well containing immobilized antibodies or antigens during an incubation step. Following the incubation, antibodies to human lactoferrin or polyvalent antibodies to human immunoglobulin coupled to horseradish peroxidase enzyme (conjugate) is added and allowed to bind to captured lactoferrin or ANCA or ASCA. Unbound conjugate is washed from the well and one component substrate (tetra-methyl-benzidene and hydrogen peroxide) is added for color development. Following the substrate incubation, the reaction is stopped by acidification and the optical density (OD) is determined spectrophotometrically at 450 nm.

The particular embodiments described herein are intended in all respects to be illustrative rather than restrictive. Alternative embodiments will become apparent to those skilled in the art to which the present invention pertains without departing from its scope.

EXAMPLE 1

Lactoferrin Qualitative Assay a. Establishment of Optimal Sample Dilution Factor and Optical Density The assay of the present invention was designed and developed to detect levels of fecal lactoferrin at a lower level detectable by predicate devices, specifically the LEUKO-TEST®. The lower limit of detection of the LEUKO-TEST® is 256 ng/mL with purified human lactoferrin. In the LEUKO-TEST®, a specimen dilution of 1:50 and a minimum limit of detection of 256 ng/mL provides a lower limit of detection in fecal specimens of approximately 12 µg/mL. A specimen dilution of 1:400 and a minimum detection limit for the assay of the present invention of 32 ng/mL also provides a lower limit of detection in fecal specimens of approximately 12 µg/mL. Accordingly, a 1:400 specimen dilution was chosen for the assay of the present invention. Similarly, an optical density of 0.200 $OD_{450}$ for the assay was chosen. (As used herein, $OD_{450}$ indicates an optical density obtained spectrophotometrically at 450 nm on a single wavelength spectrophotometer.)

It will be understood and appreciated by those of skill in the art that the preferred dilution factor and optical densities have been determined based upon reagents currently available and deemed to be optimal. However, reagents other than those now desired may become improved and desirable over time. Variations in reagents may produce preferable/optimal dilution factors and/or optical densities other than those determined herein. Such variations are contemplated to be within the scope of the present invention. The key to determining optimal values is based upon sensitivity as more fully described below.

To verify that the 1:400 specimen dilution provides the most desirable sensitivity with the current reagents, 121 fecal specimens were analyzed comparing a 1:400 dilution to a 1:800 dilution. (Sensitivity is calculated herein by dividing the number of samples taken from subjects with IBD which produce a positive result in the assay by the number of samples taken from subjects with IBD.) Test results additionally were evaluated comparing $OD_{450}$ values of 0.200 to $OD_{450}$ values of 0.300. Results were compared with microscopy for fecal leukocytes and with the LEUKO-TEST®. The results are summarized in Tables 1-8 below.

TABLE 1

Comparison of the ELISA with microscopy for fecal leukocytes using a 1:400 dilution and an $OD_{450}$ of 0.200

| ELISA vs. Microscopy (N = 121) | Microscopy positive | Microscopy negative |
|---|---|---|
| ELISA positive | 32 | 42 |
| ELISA negative | 2 | 45 |
| Relative Sensitivity | | 94.0% |
| Relative Specificity | | 52.0% |
| Correlation | | 64.0% |

TABLE 2

Comparison of the ELISA with microscopy for fecal leukocytes using a 1:400 dilution and an $OD_{450}$ of 0.300

| ELISA vs. microscopy (N = 121) | Microscopy positive | Microscopy negative |
|---|---|---|
| ELISA positive | 31 | 31 |
| ELISA negative | 3 | 56 |
| Relative Sensitivity | | 91.0% |
| Relative Specificity | | 64.0% |
| Correlation | | 72.0% |

TABLE 3

Comparison of the ELISA with microscopy for fecal leukocytes using a 1:800 dilution and an $OD_{450}$ of 0.200

| ELISA vs. microscopy (N = 121) | Microscopy positive | Microscopy negative |
|---|---|---|
| ELISA positive | 30 | 31 |
| ELISA negative | 4 | 56 |
| Relative Sensitivity | | 88.0% |
| Relative Specificity | | 64.0% |
| Correlation | | 77.0% |

TABLE 4

Comparison of the ELISA with microscopy for fecal leukocytes using a 1:800 dilution and an $OD_{450}$ of 0.300

| ELISA vs. microscopy (N = 121) | Microscopy positive | Microscopy negative |
|---|---|---|
| ELISA positive | 26 | 24 |
| ELISA negative | 8 | 63 |
| Relative Sensitivity | | 77.0% |
| Relative Specificity | | 72.0% |
| Correlation | | 74.0% |

TABLE 5

Comparison of the ELISA with the LEUKO-TEST ® using a 1:400 dilution and an $OD_{450}$ of 0.200

| ELISA vs. LEUKO-TEST ® (N = 121) | LEUKO-TEST ® Positive | LEUKO-TEST ® negative |
|---|---|---|
| ELISA positive | 43 | 31 |
| ELISA negative | 5 | 42 |
| Relative Sensitivity | | 89.6% |
| Relative Specificity | | 57.5% |
| Correlation | | 70.2% |

TABLE 6

Comparison of the ELISA with the LEUKO-TEST ® using a 1:400 dilution and an $OD_{450}$ of 0.300

| ELISA vs. LEUKO-TEST ® (N = 121) | LEUKO-TEST ® Positive | LEUKO-TEST ® negative |
|---|---|---|
| ELISA positive | 41 | 21 |
| ELISA negative | 7 | 52 |
| Relative Sensitivity | | 85.0% |
| Relative Specificity | | 71.2% |
| Correlation | | 77.0% |

TABLE 7

Comparison of the ELISA with the LEUKO-TEST ® using a 1:800 dilution and an $OD_{450}$ of 0.200

| ELISA vs. LEUKO-TEST ® (N = 121) | LEUKO-TEST ® Positive | LEUKO-TEST ® negative |
|---|---|---|
| ELISA positive | 39 | 22 |
| ELISA negative | 9 | 51 |
| Relative Sensitivity | | 81.3% |
| Relative Specificity | | 69.9% |
| Correlation | | 74.4% |

TABLE 8

Comparison of the ELISA with the LEUKO-TEST ® using a 1:800 dilution and an $OD_{450}$ of 0.300

| ELISA vs. LEUKO-TEST ® (N = 121) | LEUKO-TEST ® Positive | LEUKO-TEST ® negative |
|---|---|---|
| ELISA positive | 34 | 16 |
| ELISA negative | 14 | 57 |
| Relative Sensitivity | | 70.8% |
| Relative Specificity | | 78.1% |
| Correlation | | 75.2% |

In summary, a fecal specimen dilution of 1:400 and an assay $OD_{450}$ of 0.200 showed the highest level of sensitivity with the current reagents. Accordingly, these conditions were determined to be optimal for the assay of the present invention. Normal fecal specimens contain low levels of lactoferrin and the 1:400 dilutions have been determined to be optimal in detecting an increase in lactoferrin over background levels. The use of dilutions lower than 1:400 may result in positive test results due to the presence of normal lactoferrin levels.

b. Collection of Specimens and Preparation of Dilutions

Standard collection and handling procedures typically used for fecal specimens for culture may be used in collecting samples for the assay of the present invention. In the preferred embodiment, fecal specimens are to be tested within twenty-four hours of collection. However, if the assay is not to be performed within forty-eight hours of collection, it is preferred that the specimens be stored at −20° C. or lower. Additionally, it is preferred that collected specimens be transported and diluted in the Diluent as soon as possible after collection and, once diluted, that the specimens be stored at between about 2° C. and about 8° C. It is preferred that specimens be mixed (i.e., using a vortex mixer) thoroughly prior to performing the assay of the present invention. This includes complete mixing of the specimen prior to transfer to the Diluent, as more fully described below, as well as complete mixing of the diluted specimen prior to performing the assay.

The following method was used to prepare a diluted specimen from a liquid fecal specimen. Two plastic tubes were set up for each specimen to be tested. For each specimen, 950 µL of 1× Diluent (prepared as more fully described below) subsequently was added to each of the two tubes. Using a transfer pipette, one drop (i.e., approximately 50 µL) of liquid fecal specimen was added to one of the tubes and thoroughly mixed using a vortex mixer. Subsequently, one drop of the diluted specimen was transferred into the second tube containing 950 µL of 1× Diluent (prepared as more fully described below). The result was a 1:400 dilution of the specimen in the second tube. Thus, only the second tube was used for the remainder of the test procedure.

The following method was used to prepare a diluted specimen from a formed or solid fecal specimen. Two plastic tubes were set up for each specimen to be tested. For each specimen, 1.9 mL of 1× Diluent (prepared as more fully described below) was added to only one of the two tubes. Subsequently, 0.10 g of fecal specimen were added to this tube (1:10) and thoroughly mixed using a vortex mixer. Next, 950 µL of the 1× Diluent (prepared as more fully described below) was added to the second tube and one drop (i.e., approximately 50 µL) of the previously diluted specimen is transferred into the second tube. The result was a 1:400 dilution of the specimen in the second tube. Thus, only the second tube was used for the remainder of the test procedure.

The specimen in the second tube prepared according to either of the above procedures was mixed in a vortex mixer for approximately ten seconds and subsequently stored at between about 2° C. and about 8° C. until the remainder of the test procedure was performed. Prior to transferring the diluted specimen into a microtiter well according to the test procedure, as more fully described below, the specimen was thoroughly mixed in the vortex mixer once again. This procedure sought to ensure thorough mixing of the specimen.

c. Necessary Test Reagents and Preparation Thereof

A number of reagents were necessary to carry out the preferred embodiment of the qualitative assay of the present invention. These reagents included 10× Diluent, 1× Diluent, Conjugate, Substrate, Positive Control, Wash Buffer Solution and Stop Solution. The 10× Diluent was a 10× concentrate of buffered protein solution containing 0.2% thimerosal as a preservative. The Diluent was supplied as a 10× concentrate. Therefore, to prepare the 1× Diluent necessary for the assay of the present invention, a total volume of 400 mL was diluted by adding 40 mL of the 10× concentrate to 360 mL of deionized water. Any unused 1× Diluent was stored at between about 2° C. and about 8° C.

The Conjugate used with the assay of the present invention preferably comprises rabbit polyclonal antibody specific for human lactoferrin conjugated to horseradish peroxidase and in a buffered protein solution containing 0.02% thimerosal as a preservative. The Substrate used with the assay of the present invention preferably comprises a solution containing tetra-methyl-benzidine substrate and peroxidase. The Positive Control used with the assay of the present invention preferably comprises human lactoferrin in a buffered protein solution containing 0.02% thimerosal as a preservative. The Stop Solution used with the assay of the present invention preferably comprises 0.6 N sulfuric acid.

The Wash Buffer Solution used with the assay of the present invention was supplied as a 20× concentrate containing phosphate buffered saline, detergent and 0.2% thimerosal as a preservative. To prepare the 1× Wash Solution necessary for the assay of the present invention, a total volume of one liter of concentrate was diluted by adding 50 mL of the concentrate to 950 mL of deionized water. Any unused 1× Wash Solution was stored at between about 2° C. and about 8° C.

Microassay plates containing twelve strips and eight wells per strip are preferred for the assay of the present invention. Each specimen and each control requires a single coated well. To prepare the plates, each strip was coated with purified polyclonal antibody specific for lactoferrin. Microassay plates were stored with desiccant.

All reagents were stored at room temperature prior to use in the assay of the present invention.

The present invention includes a kit designed and prepared for carrying out the quantitative assay. In the preferred embodiment, the kit contains 40 mL 10× Diluent, 7 mL Conjugate, 14 mL Substrate, 3.5 mL Positive Control, 50 mL Wash Buffer Solution, 7 mL Stop Solution and one microassay plate stored with desiccant. The assay of the present invention utilizes antibodies to human lactoferrin. The microassay plate supplied with the kit contains immobilized polyclonal antibody against lactoferrin. The detecting antibody consists of polyclonal antibody conjugated to horseradish peroxidase.

d. Test Procedure

To perform the qualitative assay of the present invention, initially the number of wells needed was determined. Each specimen or control required one well and, therefore, the number of wells was determined accordingly. Next, one drop (i.e., about 50 µL) of Positive Control was added to a single well designated the Positive Control Well and one drop (i.e., about 50 µL) of 1× Diluent was added to a single well designated the Negative Control Well. Subsequently, two drops (i.e., about 100 µL) of 1:400 diluted specimen (prepared according to the above procedure) was added to a third well and all wells were incubated at about 37° C. (±2° C.) for approximately thirty minutes. After incubation, the contents of the assay wells was discarded into a discard pan.

Next, each well was washed using 1× Wash Solution (prepared as described above) and placed in a squirt bottle with a fine-tipped nozzle. In this manner, the 1× Wash Solution was directed into the bottom of each of the wells with some force. Each well was filled with the 1× Wash Solution and the contents thereof subsequently discarded into a discard pan. The microassay plate was then inverted and slapped on a dry paper towel. This wash procedure was performed a minimum of four times using a dry paper towel each time. If any particulate matter was observed in the wells, the washing procedure was continued until all the matter was removed.

Subsequently, one drop (i.e., about 50 µL) of Conjugate was added to each well and the wells were incubated at about 37° C. (±2° C.) for approximately thirty minutes. After incubation, the contents of the assay wells were discarded into a discard pan and the washing procedure was repeated. Next, two drops (i.e., about 100 µL) of Substrate were added to each well and the wells were gently tapped to mix the contents. The wells were then incubated at room temperature for approximately fifteen minutes. The wells were gently tapped a couple of times during the incubation period.

Next, one drop (i.e., 50 µL) of Stop Solution was added to each well and the wells were gently tapped. The wells were allowed to sit at room temperature for about two minutes before reading. The addition of Stop Solution converted the blue color to a yellow color which could then be quantified by measuring the optical density at 450 nm on a microplate ELISA reader. The instrument was blanked against the negative control and the underside of each well was wiped before measuring the optical density. Optical densities ($OD_{450}$ and $OD_{450/620}$) were recorded for the Positive Control Well, the Negative Control Well and each specimen tested. ("$OD_{450/620}$" as used herein indicates an optical density obtained spectrophotometrically at 450/620 nm on a dual wavelength spectrophotometer.) Readings of duplicate wells were averaged before the results were interpreted.

The specified test procedure represents the preferred embodiment as optimal results are obtained by following the procedure specified because the reagents, concentrations, incubation conditions, and processing specifications have been optimized for sensitivity and specificity. Accordingly, alterations of the specified procedure and/or of the indicated test conditions may affect the sensitivity and specificity of the test.

e. Quality Control

The positive and negative control must meet certain criteria for the test to be valid. First of all, the Positive Control Well must be a visible yellow color and, when read on a spectrophotometer, it must have an $OD_{450}$ and $OD_{450/620}$>0.500. The Negative Control Well must have an $OD_{450}$<0.200 or an $OD_{450/620}$<0.160. To ensure that carryover has not occurred, testing should be repeated if a sample gives a weak positive result (i.e, <0.400) and is adjacent to a strong positive well.

f. Interpretation of Results

Optical densities were measured at 450 nm on a single wavelength spectrophotometer and at 450/620 nm on a dual wavelength spectrophotometer. On a single wavelength spectrophotometer, an $OD_{450}$ of less than 0.200 indicated a negative result and an $OD_{450}$ of greater than or equal to 0.200 indicated a positive result. On a dual wavelength spectrophotometer, an $OD_{450/620}$ of less than 0.160 indicated a negative result and an $OD_{450/620}$ of greater than or equal to 0.160 indicated a positive result.

A positive test result indicated the specimen contained elevated levels of lactoferrin when compared with a reference value established for healthy control subjects. A negative test result indicated the specimen did not contain elevated levels of lactoferrin relative to samples from healthy control subjects.

g. Results

One hundred forty-nine subjects having IBD were tested according to the above procedure. Seventy-seven of the subjects, or 51.7%, were male and seventy-two of them, or 48.3%, were female. The tested male to female ratio closely approximates the 1:1 ratio observed in the general IBD patient population. Ages of the subjects ranged from 3 years to 78 years and thirty-two subjects, or 22%, were 16 years of age or younger. Seventy-seven subjects, or 51.7%, had CD and seventy-two of them, or 48.3% had UC.

Thirty-one subjects having IBS were tested. Six of the subjects, or 19.3%, were male and twenty-five of them, or 80.7%, were female. The tested male to female ratio closely approximates the 1:3 ratio observed in the general IBS population. Ages of the subjects ranged from 19 years to 78 years.

Fifty-six healthy subjects also were tested as controls. Twenty-eight of the subjects, or 50%, were male and twenty-eight of them, or 50%, were female. Ages of the subjects ranged from infants to 79 years. A summary of the tested subject population is illustrated in Table 9.

TABLE 9

Summary of Subject Population

| Summary of Clinical Histories (N = 180) | Total Subjects |
|---|---|
| Total number of IBD patients | 149 |
| No. Males | 77 |
| No. Females | 72 |
| Total number of patients with CD | 77 |
| No. Males | 43 |
| No. Females | 34 |
| Total number of patients with UC | 72 |
| No. Males | 34 |
| No. Females | 38 |
| Total number of patients with irritable bowel syndrome | 31 |
| No. Males | 6 |
| No. Females | 25 |
| Total number of healthy persons | 56 |
| No. Males | 28 |
| No. Females | 28 |

Fecal specimens were collected from each enrolled subject and stored at −70° C. until tested. Sample consistencies ranged from liquid to solid, numbers for which are illustrated in Table 10 for each subject group. As can be seen, forty-five of the IBD specimens were liquid specimens, sixty-two were semi-solid specimens, and forty-two were solid specimens. One of the IBS specimens was a liquid specimen, thirteen were semi-solid specimens, and seventeen were solid specimens. All of the specimens from healthy control subjects were solid.

TABLE 10

Summary of Specimen Consistencies for Each Subject Group

| Summary of Stool Specimens (N = 236) | Total Specimens |
|---|---|
| Total number of IBD patients (CD and UC) | 149 |
| Total number of liquid specimens | 45 |
| Total number of semi-solid specimens | 62 |
| Total number of solid specimens | 42 |
| Total number of patients with IBS | 31 |
| Total number of liquid specimens | 1 |
| Total number of semi-solid specimens | 13 |
| Total number of solid specimens | 17 |
| Total number of healthy persons | 56 |
| Total number of liquid specimens | 0 |
| Total number of semi-solid specimens | 0 |
| Total number of solid specimens | 56 |

The level of fecal lactoferrin in each specimen was determined using the qualitative lactoferrin ELISA as previously described. A specimen dilution of 1:400 was used. Results were reported as positive if an optical density of greater than or equal to 0.200 was observed. Conversely, results were reported as negative if an optical density of less than 0.200 was observed.

Of the IBD subject group, ninety-two subjects had active disease and fifty-seven had inactive disease. Of the active group, a total of eighty subjects, or 87.0%, tested positive in the assay. Of the inactive group, a total of thirty-two subjects, or 56.1%, tested positive. Of the forty-one subjects having active UC, a total of thirty-six subjects, or 87.8% tested positive in the assay. Of the fifty-one subjects having active CD, forty-four, or 86.3%, tested positive. All thirty-one patients having active IBS and all fifty-six healthy control subjects tested negative in the assay. A summary of assay test results is illustrated in Table 11 and various individual comparisons are illustrated in Tables 12, 13 and 14, as more fully described below.

TABLE 11

Summary of ELISA test Results for CD, UC, Active IBS, and Healthy Control Subjects

| Clinical Assessments N = 236 | Total | ELISA Positive | ELISA Negative |
|---|---|---|---|
| Total IBD | 149 | 75.2% (112) | 24.8% (37) |
| Active | 92 | 87.0% (80) | 13.0% (12) |
| Inactive | 57 | 56.1% (32) | 43.0% (25) |
| Total CD | 77 | 77.9% (60) | 22.1% (17) |
| Active | 56 | 86.3% (44) | 13.7% (7) |
| Inactive | 26 | 61.5% (16) | 38.5% (10) |
| Total UC | 72 | 72.2% (52) | 27.7% (20) |
| Active | 41 | 87.8% (36) | 12.2% (5) |
| Inactive | 31 | 51.6% (16) | 48.4% (15) |
| Total Active IBS | 31 | 0 | 100.0% (31) |
| Total Healthy Persons | 56 | 0 | 100.0% (56) |

When distinguishing samples from active IBD subjects from subject samples having IBS or from healthy control samples, the ELISA exhibited a sensitivity of 87% and specificity of 100%. Sensitivity was calculated by dividing the number of persons having IBD and testing positive in the ELISA by the number of subjects having IBD. Specificity was calculated by dividing the number of subjects having IBD and testing positive in the ELISA by the number of subjects testing positive in the ELISA. The predictive positive and negative values were 100% and 87.9%, respectively, and the correlation was 93.3%. These results are summarized in Table 12.

TABLE 12

Statistical Evaluation using the ELISA to Distinguish Active IBD from IBS/Healthy Control Subjects

| N = 179 | Active IBD | IBS/Healthy Controls |
|---|---|---|
| ELISA positive | 80 | 0 |
| ELISA negative | 12 | 87 |
| Sensitivity | | 87.0% |
| Specificity | | 100% |
| Predictive Positive Value | | 100% |
| Predictive Negative Value | | 87.9% |
| Correlation | | 93.3% |

When distinguishing samples from active UC subjects from subject samples having IBS or from healthy control subjects, the ELISA exhibited a sensitivity of 87.8% and a specificity of 100%. The predictive positive and negative values were 100% and 94.6%, respectively, and the correlation was 96.1%. These results are summarized in Table 13.

TABLE 13

Statistical Evaluation using the ELISA to Distinguish Active UC from IBS/Healthy Control Subjects

| N = 128 | Active UC | IBS/Healthy Controls |
|---|---|---|
| ELISA positive | 36 | 0 |
| ELISA negative | 5 | 87 |
| Sensitivity | | 87.8% |
| Specificity | | 100% |

TABLE 13-continued

Statistical Evaluation using the ELISA to Distinguish Active UC from IBS/Healthy Control Subjects

| Predictive Positive Value | 100% |
|---|---|
| Predictive Negative Value | 94.6% |
| Correlation | 96.1% |

When distinguishing subject samples having active CD from subject samples having IBS or from healthy control samples, the ELISA exhibited a sensitivity of 86.3% and a specificity of 100%. The predictive positive and negative values were 100% and 92.6%, respectively, and the correlation was 94.9%. These results are summarized in Table 14.

TABLE 14

Statistical Evaluation using the ELISA to Distinguish Active CD from IBS/Healthy Control Subjects

| N = 138 | Active UC | IBS/Healthy Controls |
|---|---|---|
| ELISA positive | 44 | 0 |
| ELISA negative | 7 | 87 |
| Sensitivity | | 86.3% |
| Specificity | | 100% |
| Predictive Positive Value | | 100% |
| Predictive Negative Value | | 92.6% |
| Correlation | | 94.9% | h. Reproducibility and Precision

The inter-assay variation was determined by analyzing eight lactoferrin-negative and eight lactoferrin-positive fecal specimens over a three day period. The average % Coefficient of Variation (CV) was 23.5% for the positive specimens and 7.4% for the negative specimens. The intra-assay variation was determined by analyzing twelve fecal specimens using six replicates in one lot of kits. The intra-assay analysis ranged in % CV from 2.7 to 24.0 with an average of 8.7%.

EXAMPLE 2

Lactoferrin Quantitative Assay

In the quantitative assay of the present invention, fecal specimens preferably are serially diluted ten-fold and added to microtiter wells containing immobilized polyclonal antibodies against human lactoferrin. If endogenous lactoferrin is present, it will bind to the antibodies during an incubation at approximately 37° C. Following the incubation, conjugate comprised of polyclonal antibodies coupled to horseradish peroxidase enzyme is added and allowed to bind to captured lactoferrin. Unbound conjugate is then washed from the well and a component substrate (e.g., tetra-methyl-benzidene and hydrogen peroxide) is added for color development. Following the substrate incubation, 0.6N sulfuric acid is added to quench the reaction and the absorbance or optical density (OD) is obtained spectrophotometrically at 450 nm on a single wavelength device. Fecal lactoferrin concentrations are determined by comparison to a standard curve generated using purified human lactoferrin.

a. Preparation of Standard Curve

A 1 mg/mL stock solution of purified human lactoferrin, manufactured by Sigma Immunochemicals of St. Louis, Mo., was prepared using 10 mg of lactoferrin dissolved in 10 mL of sterile phosphate buffered saline (PBS) at pH 7.4. Serial two-fold dilutions of lactoferrin were made using the range of approximately 6 to 100 ng/mL in Diluent. For the analysis, 0.1 mL of each standard was assayed in duplicate. Optical densities ($OD_{450}$) were determined and plotted versus lactoferrin concentration to generate standard curves. The linear portion of the curve was determined by linear regression analysis using the Log-Log method (Microsoft EXCEL, Microsoft R Office). The lowest dilution of specimen that gave an $OD_{450}$ within the linear portion of the curve was used to determine the lactoferrin concentration. The final concentration was obtained by multiplying the concentration by the dilution factor.

b. Quantitative Test Procedure

In order to assess the ability of the quantitative ELISA to measure the level of fecal lactoferrin, two fecal specimens collected six weeks apart from six female and five male adults were diluted and then spiked with lactoferrin to a concentration of 25 ng/mL. The estimated lactoferrin that was determined represents the level of lactoferrin determined from a standard curve generated with the quantitative ELISA. The % Variation represents the difference between the actual amount used to spike the sample and the estimated amount. Under these conditions, the variations ranged from 1.0% to 85.8% for females and 8.8% to 47.0% for males. Results showed a higher percent variation in female adults as compared to male adults. The stool samples that showed a higher variation had higher levels of lactoferrin prior to spiking. The results are illustrated in Tables 15 and 16 below.

TABLE 15

Stool samples of female adult subjects spiked to a final concentration of 25 ng/mL

| Patient ID # | Actual Lactoferrin (ng/ML) | Estimated Lactoferrin (ng/mL) | Variation (%) |
|---|---|---|---|
| 1 | 25 | 15.4 | 38.4 |
| 2 | 25 | 22.9 | 8.5 |
| 3 | 25 | 21.8 | 12.7 |
| 4 | 25 | 28.4 | 13.5 |
| 5 | 25 | 16.2 | 35.3 |
| 6 | 25 | 15.8 | 37.0 |
| 7 | 25 | 35.5 | 41.8 |
| 8 | 25 | 46.5 | 85.8 |
| 9 | 25 | 27.7 | 10.8 |
| 10 | 25 | 32.3 | 29.1 |
| 11 | 25 | 26.1 | 4.3 |
| 12 | 25 | 25.3 | 1.0 |

TABLE 16

Stool samples of male adult subjects spiked to a final concentration of 25 ng/mL

| Patient ID # | Actual Lactoferrin (ng/mL) | Estimated Lactoferrin (ng/mL) | Variation (%) |
|---|---|---|---|
| 1 | 25 | 21.9 | 12.4 |
| 2 | 25 | 21.2 | 15.0 |
| 3 | 25 | 20.9 | 16.3 |
| 4 | 25 | 21.4 | 14.4 |
| 5 | 25 | 20.8 | 16.8 |
| 6 | 25 | 22.8 | 8.8 |
| 7 | 25 | 28.9 | 15.5 |
| 8 | 25 | 29.4 | 17.4 |
| 9 | 25 | 36.7 | 47.0 |
| 10 | 25 | 19.5 | 21.9 |

A second method for spiking was using the same two stool specimens collected six weeks apart from six female and five male adults were diluted and spiked with lactoferrin to a concentration of 4 µg/mL. The estimated lactoferrin represents the level of lactoferrin determined from a standard curve generated by the quantitative ELISA. The % Variation represents the difference between the actual amount used to spike the sample and the estimated value. Under these conditions, the variation ranged from 11.3% to 84.9% for females and from 5.0% to 39.2% for males. Results were similar to those obtained with specimens spiked with 25 ng/mL lactoferrin as described above, showing a higher percent variation in female adults compared to male adults. The results are illustrated in Tables 17 and 18 below.

TABLE 17

Stool samples of female adult subjects spiked to a final concentration of 4 µg/mL

| Patient ID # | Actual Lactoferrin (µg/mL) | Estimated Lactoferrin (µg/mL) | Variation (%) |
|---|---|---|---|
| 1 | 4 | 4.5 | 11.3 |
| 2 | 4 | 4.6 | 15.3 |
| 3 | 4 | 5.3 | 33.4 |
| 4 | 4 | 4.9 | 21.4 |
| 5 | 4 | 3.5 | 11.5 |
| 6 | 4 | 3.4 | 14.7 |
| 7 | 4 | 5.3 | 32.7 |
| 8 | 4 | 6.7 | 67.6 |
| 9 | 4 | 5.5 | 38.6 |
| 10 | 4 | 5.8 | 44.9 |
| 11 | 4 | 5.8 | 43.9 |
| 12 | 4 | 7.4 | 84.9 |

TABLE 18

Stool samples of male adult subjects spiked to a final concentration of 4 µg/mL

| Patient ID # | Actual Lactoferrin (µg/mL) | Estimated Lactoferrin (µg/mL) | Variation (%) |
|---|---|---|---|
| 1 | 4 | 4.7 | 17.5 |
| 2 | 4 | 4.6 | 14.4 |
| 3 | 4 | 4.2 | 5.0 |
| 4 | 4 | 5.6 | 39.2 |
| 5 | 4 | 4.2 | 5.9 |
| 6 | 4 | 4.7 | 18.5 |
| 7 | 4 | 4.7 | 16.5 |
| 8 | 4 | 5.5 | 37.9 |
| 9 | 4 | 5.3 | 33.6 |
| 10 | 4 | 4.3 | 6.6 |

Monitoring Using the Quantitative ELISA

The quantitative ELISA of the present invention was used to follow the lactoferrin levels of single patient suffering from ulcerative colitis during a flare of active disease through remission. The patient showed extremely high levels of lactoferrin (e.g., 9749.37 µg/mL feces) during the peak of the active disease, the levels dropping rapidly (e.g., to 7.42 µg/mL feces) following anti-inflammatory drug therapy. Levels elevated dramatically again during a relapse and leveled at slightly above those of healthy control persons (e.g., 11.06 µg/mL feces) during periods of remission. Thus, lactoferrin levels determined according to the quantitative ELISA of the present invention accurately depicted disease activity in response to medical treatment.

EXAMPLE 3

ASCA Assay

In this example, a fecal sample was obtained and serially diluted 20 fold. 100 μl of the diluted sample was added to a test well of a microassay plate coated with extract of *Saccharomyces cerevisiae*. The sample then was incubated at 37° C. to allow antibodies to *Saccharomyces cerevisiae* to bind to the extract of *Saccharomyces cerevisiae*. Following incubation, anti-human Ig polyclonal antibodies coupled to horseradish peroxidase enzyme (conjugate) were added to the test well and allowed to bind to captured ASCA. Unbound conjugate then was washed from the well and one component substrate (tetra-methyl-benzidene and hydrogen peroxide) was added for color development. Following the substrate incubation, 0.1M sulfuric acid was added to quench the reaction and the optical density (OD) was obtained spectrophotometrically at 450 nm using a single wavelength spectrophotometer.

The method described above was used in a clinical study to test a total of 86 IBD patients (55.8% males and 44.2% females). The approximate 1 to 1 ratio of males to females was similar to the ratio observed in IBD patient populations. The IBS patient group ranged in age from 19 to 78 years and was 9% male and 91% female. This ratio of males to females (1:10) reflects the increased incidence for IBS in females as seen in patient populations. The healthy control (HC) patient group ranged in age from 20 to 79 years old and was 33.3% male and 66.6% female. A summary of the patient population in the clinical study is shown in Table 19.

TABLE 19

Summary of patient population.

| Summary of Clinical Histories (N = 120) | Total Subjects |
|---|---|
| Total number of IBD patients | 86 |
| No. Males | 48 |
| No. Females | 38 |
| Total number of patients with Crohn's Disease | 49 |
| No. Males | 26 |
| No. Females | 23 |
| Total number of patients with ulcerative colitis | 37 |
| No. Males | 22 |
| No. Females | 15 |
| Total number of patients with irritable bowel syndrome | 22 |
| No. Males | 2 |
| No. Females | 20 |
| Total number of healthy controls | 12 |
| No. Males | 4 |
| No. Females | 8 |

In the clinical study, there were 37 ulcerative colitis patients, 49 Crohn's disease patients, 22 irritable bowel patients, and 12 healthy controls. Fecal samples were collected from each enrolled subject and stored at −70° C. until tested. The optical densities for each sample were determined using the method described above. Results were reported as positive for fecal ASCA if an optical density of greater than or equal to 0.200 was observed. Results were reported as negative for fecal ASCA if an optical density of less than or equal to 0.199 was observed. Other clinical data, such as stool consistency, was also determined. Table 20, below, contains the clinical data and test results for healthy patients that participated in this clinical study. Table 21, below, contains the clinical data and test results for patients with ulcerative colitis patients that participated in this clinical study. Table 22, below, contains the clinical data and test results for patients with Crohn's disease that participated in this study. Table 23, below, contains the clinical data and test results for patients with irritable bowel syndrome that participated in this study.

TABLE 20

Clinical data and test results for healthy controls

| Donor ID | Sex | Age Range | Previous of chronic GI illness | Stool Consistency | Optical Density | Fecal ASCA |
|---|---|---|---|---|---|---|
| HC1 | F | 40-49 | NO | Solid | 0.098 | NEGATIVE |
| HC2 | F | 40-49 | NO | Solid | 0.089 | NEGATIVE |
| HC3 | M | 70-79 | NO | Solid | 0.095 | NEGATIVE |
| HC4 | F | 60-69 | NO | Solid | 0.085 | NEGATIVE |
| HC5 | M | 70-79 | NO | Solid | 0.083 | NEGATIVE |
| HC6 | F | 70-79 | NO | Solid | 0.076 | NEGATIVE |
| HC7 | F | 50-59 | NO | Solid | 0.124 | NEGATIVE |
| HC8 | F | 40-49 | NO | Solid | 0.095 | NEGATIVE |
| HC9 | F | 50-49 | NO | Solid | 0.111 | NEGATIVE |
| HC10 | F | 40-49 | NO | Solid | 0.111 | NEGATIVE |
| HC11 | M | 50-60 | NO | Solid | 0.070 | NEGATIVE |
| HC12 | M | 50-60 | NO | Solid | 0.054 | NEGATIVE |

TABLE 21

Clinical data and test results for ulcerative colitis patients

| Patient ID | Sex | Age | Disease | Stool Consistency | Disease Activity | Optical Density | Fecal ASCA |
|---|---|---|---|---|---|---|---|
| UC1 | F | 46 | UC | Liquid | ACTIVE | 0.184 | NEGATIVE |
| UC2 | M | 39 | UC | Liquid | ACTIVE | 0.378 | POSITIVE |
| UC3 | F | 30 | UC | Semi-Solid | ACTIVE | 0.193 | NEGATIVE |
| UC4 | F | 31 | UC | Semi-Solid | INACTIVE | 0.319 | POSITIVE |
| UC5 | F | 30 | UC | Semi-Solid | ACTIVE | 0.114 | NEGATIVE |
| UC6 | M | 61 | UC | Semi-Solid | INACTIVE | 0.115 | NEGATIVE |
| UC7 | F | 68 | UC | Liquid | INACTIVE | 0.091 | NEGATIVE |
| UC8 | F | 45 | UC | Liquid | ACTIVE | 0.356 | POSITIVE |
| UC9 | F | 21 | UC | Semi-Solid | ACTIVE | 0.082 | NEGATIVE |
| UC10 | F | 27 | UC | Liquid | ACTIVE | 0.161 | NEGATIVE |

TABLE 21-continued

Clinical data and test results for ulcerative colitis patients

| Patient ID | Sex | Age | Disease | Stool Consistency | Disease Activity | Optical Density | Fecal ASCA |
|---|---|---|---|---|---|---|---|
| UC11 | F | 24 | UC | Solid | INACTIVE | 0.104 | NEGATIVE |
| UC12 | F | 74 | UC | Semi-Solid | INACTIVE | 0.091 | NEGATIVE |
| UC13 | M | 69 | UC | Semi-Solid | ACTIVE | 0.070 | NEGATIVE |
| UC14 | M | 19 | UC | Solid | INACTIVE | 0.088 | NEGATIVE |
| UC15 | M | 62 | UC | Solid | INACTIVE | 0.054 | NEGATIVE |
| UC16 | F | 70 | UC | Solid | INACTIVE | 0.056 | NEGATIVE |
| UC17 | M | 23 | UC | Liquid | ACTIVE | 0.573 | POSITIVE |
| UC18 | F | 52 | UC | Solid | ACTIVE | 0.073 | NEGATIVE |
| UC19 | M | 60 | UC | Solid | INACTIVE | 0.062 | NEGATIVE |
| UC20 | F | 52 | UC | Liquid | ACTIVE | 0.089 | NEGATIVE |
| UC21 | M | 31 | UC | Solid | INACTIVE | 0.064 | NEGATIVE |
| UC22 | M | 44 | UC | Semi-Solid | INACTIVE | 0.143 | NEGATIVE |
| UC23 | F | 30 | UC | Liquid | ACTIVE | 0.110 | NEGATIVE |
| UC24 | M | 48 | UC | Semi-Solid | INACTIVE | 0.096 | NEGATIVE |
| UC25 | F | 37 | UC | Liquid | ACTIVE | 0.282 | POSITIVE |
| UC26 | F | 32 | UC | Solid | ACTIVE | 0.107 | NEGATIVE |
| UC27 | F | 46 | UC | Liquid | ACTIVE | 0.199 | NEGATIVE |
| UC28 | M | 49 | UC | Semi-Solid | INACTIVE | 0.161 | NEGATIVE |
| UC29 | F | 42 | UC | Solid | INACTIVE | 0.080 | NEGATIVE |
| UC30 | F | 41 | UC | Semi-Solid | INACTIVE | 0.087 | NEGATIVE |
| UC31 | F | 43 | UC | Solid | INACTIVE | 0.070 | NEGATIVE |
| UC32 | M | 30 | UC | Solid | ACTIVE | 0.103 | NEGATIVE |
| UC33 | F | 43 | UC | Solid | INACTIVE | 0.092 | NEGATIVE |
| UC34 | F | 33 | UC | Semi-Solid | INACTIVE | 0.075 | NEGATIVE |
| UC35 | M | 58 | UC | Semi-Solid | ACTIVE | 0.121 | NEGATIVE |
| UC36 | F | 32 | UC | Semi-Solid | ACTIVE | 0.083 | NEGATIVE |

TABLE 22

Clinical Data and test results for Crohn's disease patients.

| Patient ID | Sex | Age | Disease | Stool Consistency | Disease Activity | Optical Density | Fecal ASCA |
|---|---|---|---|---|---|---|---|
| CD1 | M | 26 | CD | Liquid | INACTIVE | 1.900 | POSITIVE |
| CD2 | M | 60 | CD | Liquid | ACTIVE | 2.849 | POSITIVE |
| CD3 | F | 66 | CD | Liquid | ACTIVE | 0.282 | POSITIVE |
| CD4 | F | 74 | CD | Semi-Solid | INACTIVE | 0.091 | NEGATIVE |
| CD5 | F | 25 | CD | Solid | INACTIVE | 0.162 | NEGATIVE |
| CD6 | F | 66 | CD | Semi-Solid | INACTIVE | 1.240 | POSITIVE |
| CD7 | M | 39 | CD | No Data | ACTIVE | 1.150 | POSITIVE |
| CD8 | F | 46 | CD | Liquid | ACTIVE | 0.160 | NEGATIVE |
| CD9 | F | 46 | CD | Semi-Solid | INACTIVE | 0.074 | NEGATIVE |
| CD10 | F | 56 | CD | Solid | ACTIVE | 0.406 | POSITIVE |
| CD11 | M | 56 | CD | Solid | ACTIVE | 0.168 | NEGATIVE |
| CD12 | F | 56 | CD | Liquid | ACTIVE | 0.732 | POSITIVE |
| CD13 | M | 21 | CD | Solid | ACTIVE | 1.369 | POSITIVE |
| CD14 | M | 52 | CD | Semi-Solid | INACTIVE | 0.136 | NEGATIVE |
| CD15 | M | 63 | CD | Solid | INACTIVE | 0.134 | NEGATIVE |
| CD16 | M | 34 | CD | Solid | ACTIVE | 0.076 | NEGATIVE |
| CD17 | F | 45 | CD | Semi-Solid | ACTIVE | 0.160 | NEGATIVE |
| CD18 | M | 67 | CD | Semi-Solid | INACTIVE | 0.059 | NEGATIVE |
| CD19 | F | 46 | CD | No Data | ACTIVE | 0.839 | POSITIVE |
| CD20 | M | 66 | CD | Semi-Solid | INACTIVE | 0.084 | NEGATIVE |
| CD21 | M | 63 | CD | Liquid | ACTIVE | 0.780 | POSITIVE |
| CD21 | M | 51 | CD | Semi-Solid | ACTIVE | 3.000 | POSITIVE |
| CD22 | M | 34 | CD | Semi-Solid | ACTIVE | 1.447 | POSITIVE |
| CD23 | M | 21 | CD | Solid | ACTIVE | 2.757 | POSITIVE |
| CD24 | F | 78 | CD | Semi-Solid | INACTIVE | 0.092 | NEGATIVE |
| CD25 | F | 27 | CD | Semi-Solid | ACTIVE | 0.979 | POSITIVE |
| CD26 | M | 40 | CD | Liquid | ACTIVE | 0.373 | POSITIVE |
| CD27 | M | 51 | CD | Liquid | ACTIVE | 0.978 | POSITIVE |
| CD28 | M | 42 | CD | Liquid | ACTIVE | 0.089 | NEGATIVE |
| CD29 | F | 31 | CD | Solid | INACTIVE | 0.075 | NEGATIVE |
| CD30 | F | 59 | CD | Solid | ACTIVE | 0.088 | NEGATIVE |
| CD31 | M | 35 | CD | Semi-Solid | ACTIVE | 1.487 | POSITIVE |
| CD32 | M | 37 | CD | Semi-Solid | INACTIVE | 1.257 | POSITIVE |
| CD33 | F | 77 | CD | Solid | INACTIVE | 0.093 | NEGATIVE |
| CD34 | F | 40 | CD | No Data | ACTIVE | 1.762 | POSITIVE |
| CD35 | F | 38 | CD | Liquid | ACTIVE | 0.098 | NEGATIVE |
| CD36 | M | 51 | CD | Liquid | ACTIVE | 2.326 | POSITIVE |

TABLE 22-continued

Clinical Data and test results for Crohn's disease patients.

| Patient ID | Sex | Age | Disease | Stool Consistency | Disease Activity | Optical Density | Fecal ASCA |
|---|---|---|---|---|---|---|---|
| CD37 | M | 38 | CD | Semi-Solid | ACTIVE | 0.091 | NEGATIVE |
| CD38 | M | 37 | CD | Liquid | ACTIVE | 0.372 | POSITIVE |
| CD39 | M | 59 | CD | Semi-Solid | ACTIVE | 0.224 | POSITIVE |
| CD40 | F | 41 | CD | Solid | ACTIVE | 0.503 | POSITIVE |
| CD41 | M | 41 | CD | Solid | ACTIVE | 0.117 | NEGATIVE |
| CD42 | M | 48 | CD | Liquid | ACTIVE | 0.115 | NEGATIVE |
| CD43 | F | 40 | CD | Solid | INACTIVE | 0.638 | POSITIVE |
| CD44 | F | 72 | CD | Solid | ACTIVE | 0.087 | NEGATIVE |
| CD45 | F | 32 | CD | Liquid | INACTIVE | 0.911 | POSITIVE |
| CD46 | F | 24 | CD | Liquid | ACTIVE | 0.341 | POSITIVE |
| CD47 | M | 23 | CD | Solid | INACTIVE | 0.088 | NEGATIVE |
| CD48 | F | 34 | CD | Liquid | ACTIVE | 0.599 | POSITIVE |

TABLE 23

Clinical data and test results for irritable bowel syndrome patients

| Patient ID | Sex | Age | Disease | Stool consistency | Disease Activity | Optical Density | Fecal ASCA |
|---|---|---|---|---|---|---|---|
| IBS1 | F | 56 | IBS | Semi-Solid | ACTIVE | 0.132 | NEGATIVE |
| IBS2 | F | 48 | IBS | Solid | ACTIVE | 0.103 | NEGATIVE |
| IBS3 | F | 30 | IBS | Solid | ACTIVE | 0.073 | NEGATIVE |
| IBS4 | F | 31 | IBS | Solid | ACTIVE | 0.074 | NEGATIVE |
| IBS5 | F | 72 | IBS | Semi-Solid | ACTIVE | 0.079 | NEGATIVE |
| IBS6 | F | 47 | IBS | Solid | ACTIVE | 0.088 | NEGATIVE |
| IBS7 | F | 19 | IBS | Semi-Solid | ACTIVE | 0.105 | NEGATIVE |
| IBS8 | F | 58 | IBS | Semi-Solid | ACTIVE | 0.107 | NEGATIVE |
| IBS9 | F | 40 | IBS | Solid | ACTIVE | 0.065 | NEGATIVE |
| IBS10 | F | 33 | IBS | Semi-Solid | ACTIVE | 0.065 | NEGATIVE |
| IBS11 | F | 78 | IBS | Solid | ACTIVE | 0.071 | NEGATIVE |
| IBS12 | F | 74 | IBS | Semi-Solid | ACTIVE | 0.063 | NEGATIVE |
| IBS13 | F | 50 | IBS | Semi-Solid | ACTIVE | 0.052 | NEGATIVE |
| IBS14 | F | 39 | IBS | Solid | ACTIVE | 0.079 | NEGATIVE |
| IBS15 | F | 54 | IBS | Solid | ACTIVE | 0.080 | NEGATIVE |
| IBS16 | M | 49 | IBS | Semi-Solid | ACTIVE | 0.238 | POSITIVE |
| IBS17 | M | 53 | IBS | Solid | ACTIVE | 0.123 | NEGATIVE |
| IBS18 | F | 34 | IBS | Solid | ACTIVE | 0.091 | NEGATIVE |
| IBS19 | F | 43 | IBS | Solid | ACTIVE | 0.075 | NEGATIVE |
| IBS20 | F | 35 | IBS | Solid | ACTIVE | 0.075 | NEGATIVE |
| IBS21 | F | 51 | IBS | Semi-Solid | ACTIVE | 0.081 | NEGATIVE |
| IBS22 | F | 40 | IBS | Solid | ACTIVE | 0.083 | NEGATIVE |

There were a total of 49 patients with Crohn's disease and 37 with ulcerative colitis. In the Crohn's disease group, a total of 55.1% patients were positive for fecal ASCA. In the ulcerative colitis group, 13.5% were positive. Of the 22 IBS patients, a single patient (4.6%) was positive for fecal ASCA. All 12 healthy controls were negative. A summary of positive results for fecal ASCA is shown in Table 24.

TABLE 24

Summary of positive results for Crohn's disease, ulcerative colitis, active IBS, and healthy controls

| Total Assessments N = 120 | Total | Fecal ASCA Positive | Fecal ASCA Negative |
|---|---|---|---|
| Total IBD (Crohn's disease and ulcerative colitis) | 86 | 37.2% (32) | 62.8% (54) |
| Total Crohn's Disease | 49 | 55.1% (27) | 44.9% (22) |
| Total Ulcerative Colitis | 37 | 13.5% (5) | 86.5% (32) |
| Total Active IBS | 22 | 4.6% (1) | 96.4% (21) |
| Total Healthy Controls | 12 | 0 | 100.0% (12) |

When distinguishing Crohn's disease from ulcerative colitis, fecal ASCA exhibited a sensitivity of 55.1% and specificity of 86.5%. The predictive positive and negative values were 84.4% and 59.3%, respectively, and the correlation was 68.6% as shown in Table 25.

TABLE 25

Statistical evaluation using the presence of fecal ASCA to distinguish Crohn's disease from ulcerative colitis

| N = 86 | Crohn's disease | Ulcerative colitis |
|---|---|---|
| Fecal ASCA positive | 27 | 5 |
| Fecal ASCA negative | 22 | 32 |
| Sensitivity | 55.1% | |
| Specificity | 86.5% | |
| Predictive Positive Value | 84.4% | |
| Predictive Negative Value | 59.3% | |
| Correlation | 68.6% | |

When distinguishing Crohn's disease from ulcerative colitis, irritable bowel syndrome and healthy controls, fecal ASCA exhibited a sensitivity of 55% and a specificity of 91.6%. The predictive positive and negative values were 82% and 75%, respectively, and the correlation was 77% as shown below in Table 26.

TABLE 26

Statistical evaluation using fecal ASCA to distinguish Crohn's disease from ulcerative colitis, irritable bowel syndrome/healthy controls

| N = 120 | Crohn's disease | UC/IBS/Healthy Controls |
|---|---|---|
| Fecal ASCA positive | 27 | 6 |
| Fecal ASCA negative | 22 | 65 |
| Sensitivity | | 55.1% |
| Specificity | | 91.6% |
| Predictive Positive Value | | 81.8% |
| Predictive Negative Value | | 74.7% |
| Correlation | | 76.7% |

The mean optical densities for each group were obtained and differences were tested for statistical significance using a two-tailed t-test giving a p-value result. Of the 33 patients that tested positive for fecal ASCA, there were 27 CD, 5 UC, and 1 IBS. Sensitivity, specificity and overall correlation were 55.1%, 91.5% and 76.7%, respectively. ASCA-positive CD showed a higher mean±SD A450 of 1.183±0.794 as compared to 0.382±0.113 for UC and the single A450 of 0.0.091±0.0.038 for IBS. There was a significant difference between CD and all other subject groups. A summary of the statistical analysis is listed in Table 27.

TABLE 27

Summary of the Mean and P values of Optical Densities for Fecal ASCA

| Test Group | Mean Optical Density | Standard Deviation | Optical Density Range | P Value |
|---|---|---|---|---|
| CD | 1.183 | 0.794 | 0.341-3.000 | CD vs UC, BS, HC $P < 0.005$ |
| UC | 0.382 | 0.113 | 0.382-0.113 | CD vs UC $P < 0.05$ |
| IBS | 0.091 | 0.038 | 0.052-0.238 | CD vs IBS $P < 0.005$ |
| HC | 0.091 | 0.019 | 0.054-0.124 | CD vs HC $P < 0.005$ |

The sensitivity of the fecal ASCA test also was determined using serial two fold dilutions of highly purified ASCA antibodies. For the analysis, standard curves were generated using the kit diluent. The test was consistently positive at a concentration of 0.62 μg/mL as determined by a cutoff absorbency value of $\geq 0.200$. Individual results are shown below in Table 28. The standard curves are shown in FIG. 1.

TABLE 28

Standard curves generated using purified ASCA antibodies

| Purified ASCA Antibodies (μg/mL) | Test 1 | Test 2 | Mean | Std Dev |
|---|---|---|---|---|
| 5.00 | 1.702 | 1.856 | 1.779 | 0.108 |
| 2.50 | 1.117 | 1.099 | 1.108 | 0.012 |
| 1.25 | 0.634 | 0.624 | 0.629 | 0.007 |
| 0.62 | 0.303 | 0.329 | 0.316 | 0.018 |
| 0.31 | 0.191 | 0.164 | 0.177 | 0.019 |
| 0.16 | 0.115 | 0.113 | 0.114 | 0.001 |
| 0.08 | 0.090 | 0.077 | 0.083 | 0.009 |
| 0.04 | 0.063 | 0.065 | 0.064 | 0.001 |

Tests also were conducted to determine what type of immunoglobulins (antibodies) were present in a fecal sample and in serum. The immunglobulin typing was done for human IgA, human $IgA_{sec}$, human IgD, human IgM, and human IgG. The immunoglobulin typing was done on a fecal sample from 6 Crohn's disease patients and 2 ulcerative colitis and on a serum control sample using pre-absorbed Ig-type specific conjugates. The serum control sample was obtained from a patient with a confirmed allergy to Saccharomyces cerevisiae.

Of the Crohn's disease patients, 5 patients exhibited a response to IgA and $IgA_{sec}$, 4 patients exhibited a response to IgM and a single patient exhibited a response to IgG. Of the 2 ulcerative colitis patients, a single patient reacted with the Ig conjugate. The serum control only exhibited a response to individual immunoglobulins IgM and IgG. A response to IgA and $IgA_{sec}$ occurred the fecal samples but not in the control serum sample. A summary of results is shown in Table 29.

TABLE 29

A Summary of Immunoglobulin Typing of ASCA in a Human Fecal sample and a Serum Control

| Patient Number | Disease | IgA Conjugate | $IgA_{sec}$ Conjugate | IgD Conjugate | IgM Conjugate | IgG Conjugate | Ig Conjugate |
|---|---|---|---|---|---|---|---|
| 1 | Crohn's Disease | + | + | − | + | + | + |
| 2 | Crohn's Disease | + | + | − | + | − | + |
| 3 | Crohn's Disease | − | − | − | − | − | − |
| 4 | Crohn's Disease | + | + | NO DATA | + | − | + |
| 5 | Crohn's Disease | + | + | NO DATA | − | − | + |

TABLE 29-continued

A Summary of Immunoglobulin Typing of ASCA
in a Human Fecal sample and a Serum Control

| Patient Number | Disease | IgA Conjugate | IgA$_{sec}$ Conjugate | IgD Conjugate | IgM Conjugate | IgG Conjugate | Ig Conjugate |
|---|---|---|---|---|---|---|---|
| 6 | Crohn's Disease | + | + | NO DATA | + | − | + |
| 7 | Ulcerative Colitis | − | − | − | − | − | − |
| 8 | Ulcerative Colitis | − | − | − | − | − | + |
| Serum Control | Yeast Allergy | − | − | − | + | + | + |

EXAMPLE 4

ANCA Assay

The ANCA specific immunoassay was used to differentiate ulcerative colitis and other gastrointestinal illnesses such as Crohn's disease and irritable bowel syndrome by measuring the level of total fecal ANCA. A qualitative immunoassay such as an enzyme-linked immunoassay that utilizes both monoclonal and polyclonal antibodies to endogenous human ANCA indicated the absence or presence of ulcerative colitis. In the example qualitative assay, the fecal specimen was diluted 10 fold and added to a well containing the immobilized neutrophil antigens. If ANCA was present, it was bound to the antigens during the incubation at 37° C. Following the incubation, anti-human Ig polyclonal antibodies coupled to horseradish peroxidase enzyme (conjugate) were added and allowed to bind to captured ANCA. Unbound conjugate was then washed from the well and one component substrate (tetramethybenzidene and hydrogen peroxide) was added for color development. Following the substrate incubation, 0.1M sulfuric acid was added to quench the reaction and the optical density (OD) was obtained spectrophotometrically at 450 nm.

Using the procedure described above, a total of 98 IBD patients were enrolled and comprised 51% males and 49% females with an age range of 0 to 69 years. The approximate 1 to 1 ratio is similar to the ratio observed in IBD patient populations. The IBS patient group had an age range of 5 to 39 years with 57% males and 43% females. The healthy controls were 55% male and 45% female and comprised the age range of 20 to 79 years. Individual numbers for each age group are shown in Table 30.

TABLE 30

Summary of patient population.

| Summary of Clinical Histories (N = 116) | Total Subjects |
|---|---|
| Total number of IBD patients | 98 |
| No. Males | 50 |
| No. Females | 48 |
| Total number of patients with Crohn's Disease | 47 |
| No. Males | 26 |
| No. Females | 21 |
| Total number of patients with ulcerative colitis | 51 |
| No. Males | 24 |
| No. Females | 27 |
| Total number of patients with irritable bowel syndrome | 7 |
| No. Males | 4 |
| No. Females | 3 |
| Total number of healthy persons | 11 |
| No. Males | 6 |
| No. Females | 5 |

There were 51 ulcerative colitis patients, 47 Crohn's disease patients, 7 irritable bowel patients, and 11 healthy adults recruited for the study. Fecal specimens were collected from each enrolled patient and stored at −70° C. until tested. Specimen consistency ranged from solid to liquid. The level of fecal ANCA was determined using the qualitative ANCA ELISA as previously described. Disease activity was defined using elevated fecal lactoferrin as an indicator of intestinal inflammation. A dilution of 1:10 was used in the ANCA-CHEK (qualitative ELISA) and results were reported as positive (absorbance values $\geq 0.140$) or negative (absorbance values <0.140). The mean optical densities, standard deviation and P values (two-tailed student T-test with unequal variance) were determined for the ANCA positive ulcerative colitis patients. Of the 26 patients that tested positive for fecal ANCA, there were 4 CD, 21 UC, and 1 healthy person. ANCA-positive UC showed a mean±SD OD$_{450}$ of 0.311±0.166. The mean OD for the UC patients was significantly different from IBS and healthy persons (p value<0.0005). A summary of the statistical analysis is listed in Table 31.

TABLE 31

Summary of the mean, standard deviation and P values for ANCA-CHEK Optical densities

| Group ID | Number | Mean Optical Density | Standard Deviation | Optical Density Range | P values |
|---|---|---|---|---|---|
| ANCA + UC | 21 | 0.311 | 0.166 | 0.141-0.804 | UC vs CD p < 0.5 |
| ANCA + CD | 4 | 0.209 | 0.115 | 0.141-0.381 | UC vs CD, IBS, H p < 0.0005 |
| IBS | 7 | 0.078 | 0.027 | 0.047-0.121 | UC vs CD, IBS p < 0.005 |

TABLE 31-continued

Summary of the mean, standard deviation and P values for ANCA-CHEK Optical densities

| Group ID | Number | Mean Optical Density | Standard Deviation | Optical Density Range | P values |
|---|---|---|---|---|---|
| Healthy | 11 | 0.071 | 0.041 | 0.039-0.104 | UC vs IBS, H $p < 0.0005$ |

In the IBD group, there were 47 with Crohn's disease and 51 with ulcerative colitis. In the ulcerative colitis group, 41% were positive. In the Crohn's disease group, a total of 9% patients were positive by the ANCA-CHEK. Of the 11 healthy persons, 1 was positive and all 7 IBS patients were negative by the ANCA-CHEK test. A summary of positive results for the ANCA-CHEK is shown in Table 32 and individual results are listed in Tables 33 through 34.

TABLE 32

Summary of positive results for Crohn's disease, ulcerative colitis, and IBS

| Total Assessments N = 116 | Total | Fecal ANCA Positive | Fecal ANCA Negative |
|---|---|---|---|
| Total IBD (Crohn's disease and ulcerative colitis) | 98 | 26% (25) | 75% (73) |
| Total Crohn's Disease | 47 | 9% (4) | 91% (43) |
| Total Ulcerative Colitis | 51 | 41% (21) | 59% (30) |
| Total IBS | 7 | 0 | 7 |
| Total Healthy Persons | 11 | 9% (1) | 91% (10) |

When distinguishing ulcerative colitis from Crohn's disease, the ANCA-CHEK exhibited a sensitivity of 41% and specificity of 92%. The predictive positive and negative values were 84% and 59%, respectively, and the correlation was 65% (Table 33).

TABLE 33

Statistical evaluation using the ANCA-CHEK to distinguish Crohn's disease from ulcerative colitis

| N = 98 | Ulcerative colitis | Crohn's disease |
|---|---|---|
| ANCA-CHEK positive | 21 | 4 |
| ANCA-CHEK negative | 30 | 43 |
| Sensitivity | | 41% |
| Specificity | | 92% |
| Predictive Positive Value | | 84% |
| Predictive Negative Value | | 59% |
| Correlation | | 65% |

When distinguishing ulcerative colitis from irritable bowel syndrome and healthy persons, the ANCA-CHEK exhibited a sensitivity of 41% and a specificity of 92%. The predictive positive and negative values were 81% and 67%, respectively, and the correlation was 70% (Table 34).

TABLE 34

Statistical evaluation using the ANCA-CHEK to distinguish ulcerative colitis from Crohn's disease, irritable bowel syndrome and healthy persons

| N = 116 | Ulcerative colitis | Crohn's disease IBS/Healthy |
|---|---|---|
| ANCA-CHEK positive | 21 | 5 |
| ANCA-CHEK negative | 30 | 60 |
| Sensitivity | | 41% |
| Specificity | | 92% |
| Predictive Positive Value | | 81% |
| Predictive Negative Value | | 67% |
| Correlation | | 70% |

Figure 2:
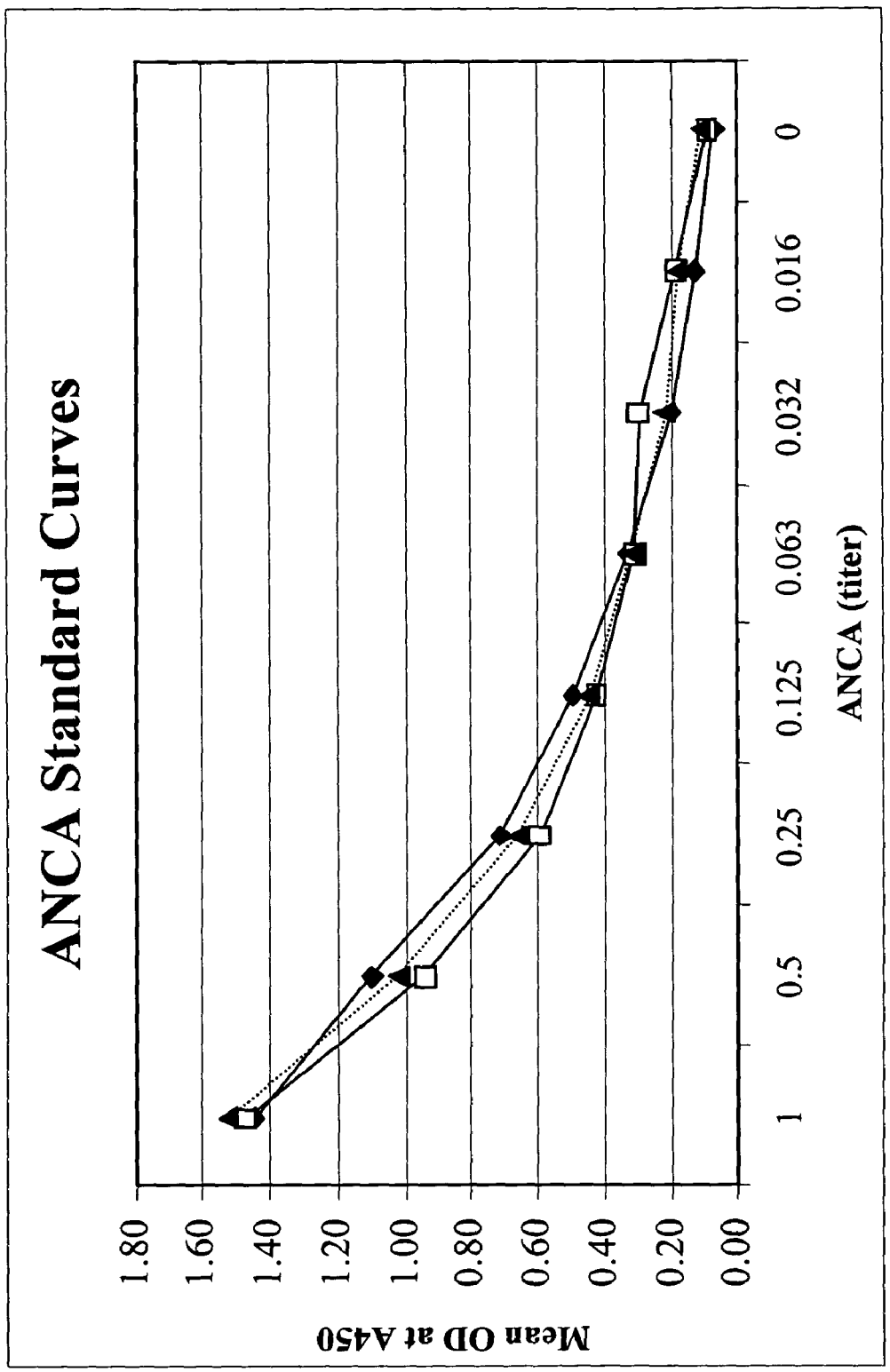
FIG. 2 is graphical representation of a standard curve of anti-neutrophil cytoplasmic antidodies in accordance with an embodiment of the present invention.

The sensitivity of the ANCA-CHEK was determined using serial two fold dilutions of human ANCA positive serum. For the analysis, standard curves were generated using the sample diluent. The test was consistently positive to a titer of 0.063 as determined by a cutoff absorbance value of $\geq 0.200$. Individual results are shown below in Table 35 and standard curves are shown in FIG. 2.

TABLE 35

Standard curves generated using ANCA-CHEK (cut-offs are bolded)

| Human ANCA Serum | Test 1 | Test 2 | Test 3 | Mean | Std Dev |
|---|---|---|---|---|---|
| 1.000 (Neat) | 1.441 | 1.469 | 1.525 | 1.478 | 0.043 |
| 0.500 | 1.098 | 0.941 | 1.014 | 1.018 | 0.079 |
| 0.250 | 0.717 | 0.595 | 0.666 | 0.659 | 0.061 |
| 0.125 | 0.492 | 0.428 | 0.444 | 0.455 | 0.033 |
| 0.063 | 0.327 | 0.303 | 0.320 | 0.317 | 0.012 |
| 0.032 | 0.196 | 0.295 | 0.221 | 0.237 | 0.051 |
| 0.016 | 0.132 | 0.184 | 0.179 | 0.165 | 0.029 |
| Diluent | 0.067 | 0.093 | 0.109 | 0.090 | 0.021 |

Table 36, below contains the clinical data and test results for patients with ulcerative colitis that participated in the study. Table 37, below, contains the clinical data and test results for patients with Crohn's disease that participated in the study. Table 38, below, contains the clinical data and test results for patients with irritable bowel syndrome that participated in the study. Table 39, below, contains the clinical data and test results for healthy patients that participated in the study.

TABLE 36

Clinical and ELISA results for ulcerative colitis patients.

| Patient ID | Sex | Age Range | Disease | Disease Activity | ANCA-CHEK $OD_{450}$ | ANCA-CHEK Result |
|---|---|---|---|---|---|---|
| UC1 | F | 10-19 | UC | INACTIVE | 0.053 | NEGATIVE |
| UC2 | F | 5-9 | UC | INACTIVE | 0.107 | NEGATIVE |
| UC3 | F | 5-9 | UC | ACTIVE | 0.058 | NEGATIVE |
| UC4 | M | 10-19 | UC | INACTIVE | 0.048 | NEGATIVE |
| UC5 | M | 10-19 | UC | ACTIVE | 0.512 | POSITIVE |
| UC6 | F | 10-19 | UC | ACTIVE | 0.061 | NEGATIVE |
| UC7 | M | 5-9 | UC | ACTIVE | 0.211 | POSITIVE |
| UC8 | M | 10-19 | UC | ACTIVE | 0.106 | NEGATIVE |
| UC9 | M | 10-19 | UC | INACTIVE | 0.804 | POSITIVE |
| UC10 | M | 10-19 | UC | ACTIVE | 0.091 | NEGATIVE |
| UC11 | F | 10-19 | UC | ACTIVE | 0.169 | POSITIVE |

TABLE 36-continued

Clinical and ELISA results for ulcerative colitis patients.

| Patient ID | Sex | Age Range | Disease | Disease Activity | ANCA-CHEK OD$_{450}$ | ANCA-CHEK Result |
|---|---|---|---|---|---|---|
| UC12 | F | 10-19 | UC | ACTIVE | 0.209 | POSITIVE |
| UC13 | F | 10-19 | UC | ACTIVE | 0.351 | POSITIVE |
| UC14 | F | 10-19 | UC | ACTIVE | 0.198 | POSITIVE |
| UC15 | F | 5-9 | UC | ACTIVE | 0.098 | NEGATIVE |
| UC16 | F | 5-9 | UC | ACTIVE | 0.050 | NEGATIVE |
| UC17 | F | 10-19 | UC | ACTIVE | 0.091 | NEGATIVE |
| UC18 | M | 10-19 | UC | ACTIVE | 0.603 | POSITIVE |
| UC19 | M | 10-19 | UC | ACTIVE | 0.091 | NEGATIVE |
| UC20 | F | 10-19 | UC | ACTIVE | 0.142 | POSITIVE |
| UC21 | M | 10-19 | UC | ACTIVE | 0.074 | NEGATIVE |
| UC22 | F | 10-19 | UC | ACTIVE | 0.105 | NEGATIVE |
| UC23 | M | 10-19 | UC | INACTIVE | 0.256 | POSITIVE |
| UC24 | F | 0-4 | UC | ACTIVE | 0.308 | POSITIVE |
| UC25 | F | 5-9 | UC | ACTIVE | 0.072 | NEGATIVE |
| UC26 | M | 10-19 | UC | INACTIVE | 0.237 | POSITIVE |
| UC27 | M | 10-19 | UC | ACTIVE | 0.048 | NEGATIVE |
| UC28 | M | 10-19 | UC | ACTIVE | 0.049 | NEGATIVE |
| UC29 | M | 10-19 | UC | ACTIVE | 0.059 | NEGATIVE |
| UC30 | F | 10-19 | UC | INACTIVE | 0.047 | NEGATIVE |
| UC31 | M | 10-19 | UC | ACTIVE | 0.055 | NEGATIVE |
| UC32 | M | 10-19 | UC | INACTIVE | 0.044 | NEGATIVE |
| UC33 | F | 10-19 | UC | ACTIVE | 0.043 | NEGATIVE |
| UC34 | M | 5-9 | UC | ACTIVE | 0.046 | NEGATIVE |
| UC35 | M | 10-18 | UC | INACTIVE | 0.043 | NEGATIVE |
| UC36 | M | 10-17 | UC | INACTIVE | 0.040 | NEGATIVE |
| UC37 | F | 10-19 | UC | ACTIVE | 0.047 | NEGATIVE |
| UC38 | F | 0-4 | UC | ACTIVE | 0.049 | NEGATIVE |
| UC39 | F | 5-9 | UC | INACTIVE | 0.363 | POSITIVE |
| UC40 | F | 10-19 | UC | INACTIVE | 0.046 | NEGATIVE |
| UC41 | M | 10-19 | UC | ACTIVE | 0.118 | NEGATIVE |
| UC42 | F | 50-59 | UC | ACTIVE | 0.230 | POSITIVE |
| UC43 | M | 10-19 | UC | ACTIVE | 0.051 | NEGATIVE |
| UC44 | F | 30-39 | UC | ACTIVE | 0.060 | NEGATIVE |
| UC45 | F | 50-59 | UC | ACTIVE | 0.465 | POSITIVE |
| UC46 | M | 50-59 | UC | ACTIVE | 0.274 | POSITIVE |
| UC47 | F | 30-39 | UC | ACTIVE | 0.141 | POSITIVE |
| UC48 | M | 60-69 | UC | ACTIVE | 0.184 | POSITIVE |
| UC49 | F | 40-49 | UC | ACTIVE | 0.397 | POSITIVE |
| UC50 | F | 40-49 | UC | ACTIVE | 0.337 | POSITIVE |
| UC51 | M | 30-39 | UC | ACTIVE | 0.143 | POSITIVE |

TABLE 37

Clinical and ELISA results for Crohn's disease patients.

| Patient ID | Sex | Age Range | Disease | Disease Activity | ANCA-CHEK OD$_{450}$ | ANCA-CHEK Result |
|---|---|---|---|---|---|---|
| CD1 | M | 10-19 | CD | ACTIVE | 0.050 | NEGATIVE |
| CD2 | M | 10-19 | CD | ACTIVE | 0.113 | NEGATIVE |
| CD3 | M | 10-19 | CD | ACTIVE | 0.050 | NEGATIVE |
| CD4 | F | 10-19 | CD | ACTIVE | 0.381 | POSITIVE |
| CD5 | F | 10-19 | CD | ACTIVE | 0.058 | NEGATIVE |
| CD6 | M | 10-19 | CD | INACTIVE | 0.068 | NEGATIVE |
| CD7 | M | 10-19 | CD | ACTIVE | 0.066 | NEGATIVE |
| CD8 | M | 5-9 | CD | ACTIVE | 0.059 | NEGATIVE |
| CD9 | F | 10-19 | CD | ACTIVE | 0.059 | NEGATIVE |
| CD10 | F | 10-19 | CD | ACTIVE | 0.065 | NEGATIVE |
| CD11 | F | 10-19 | CD | INACTIVE | 0.055 | NEGATIVE |
| CD12 | M | 10-19 | CD | INACTIVE | 0.071 | NEGATIVE |
| CD13 | F | 10-19 | CD | ACTIVE | 0.065 | NEGATIVE |
| CD14 | M | 10-19 | CD | ACTIVE | 0.098 | NEGATIVE |
| CD15 | F | 10-19 | CD | ACTIVE | 0.099 | NEGATIVE |
| CD16 | M | 10-19 | CD | ACTIVE | 0.166 | POSITIVE |
| CD17 | F | 10-19 | CD | ACTIVE | 0.147 | POSITIVE |
| CD18 | M | 10-19 | CD | ACTIVE | 0.057 | NEGATIVE |
| CD19 | F | 10-19 | CD | ACTIVE | 0.084 | NEGATIVE |
| CD20 | M | 10-19 | CD | ACTIVE | 0.053 | NEGATIVE |
| CD21 | F | 10-19 | CD | ACTIVE | 0.074 | NEGATIVE |

TABLE 37-continued

Clinical and ELISA results for Crohn's disease patients.

| Patient ID | Sex | Age Range | Disease | Disease Activity | ANCA-CHEK OD$_{450}$ | ANCA-CHEK Result |
|---|---|---|---|---|---|---|
| CD22 | M | 10-19 | CD | ACTIVE | 0.054 | NEGATIVE |
| CD23 | M | 0-5 | CD | ACTIVE | 0.055 | NEGATIVE |
| CD24 | M | 10-19 | CD | ACTIVE | 0.067 | NEGATIVE |
| CD25 | M | 10-19 | CD | ACTIVE | 0.099 | NEGATIVE |
| CD26 | M | 5-9 | CD | ACTIVE | 0.086 | NEGATIVE |
| CD27 | F | 10-19 | CD | ACTIVE | 0.043 | NEGATIVE |
| CD28 | F | 10-19 | CD | ACTIVE | 0.064 | NEGATIVE |
| CD29 | M | 5-9 | CD | INACTIVE | 0.039 | NEGATIVE |
| CD30 | M | 10-19 | CD | ACTIVE | 0.071 | NEGATIVE |
| CD31 | F | 10-15 | CD | ACTIVE | 0.109 | NEGATIVE |
| CD32 | M | 10-19 | CD | INACTIVE | 0.057 | NEGATIVE |
| CD33 | M | 10-19 | CD | ACTIVE | 0.141 | POSITIVE |
| CD34 | M | 10-19 | CD | INACTIVE | 0.045 | NEGATIVE |
| CD35 | F | 10-19 | CD | ACTIVE | 0.051 | NEGATIVE |
| CD36 | F | 10-19 | CD | ACTIVE | 0.132 | NEGATIVE |
| CD37 | F | 10-19 | CD | INACTIVE | 0.046 | NEGATIVE |
| CD38 | M | 10-19 | CD | ACTIVE | 0.057 | NEGATIVE |
| CD39 | F | 20-29 | CD | INACTIVE | 0.051 | NEGATIVE |
| CD40 | F | 20-29 | CD | ACTIVE | 0.053 | NEGATIVE |
| CD41 | M | 50-59 | CD | ACTIVE | 0.060 | NEGATIVE |
| CD42 | F | 50-59 | CD | ACTIVE | 0.062 | NEGATIVE |
| CD43 | M | 20-29 | CD | ACTIVE | 0.056 | NEGATIVE |
| CD44 | F | 60-69 | CD | ACTIVE | 0.130 | NEGATIVE |
| CD45 | M | 60-69 | CD | ACTIVE | 0.078 | NEGATIVE |
| CD46 | F | 40-49 | CD | ACTIVE | 0.116 | NEGATIVE |
| CD47 | M | 60-69 | CD | ACTIVE | 0.057 | NEGATIVE |

TABLE 38

Clinical and ELISA results for Irritable bowel syndrome patients.

| Patient ID | Sex | Age Range | Disease | ANCA-CHEK OD$_{450}$ | ANCA-CHEK Results |
|---|---|---|---|---|---|
| IBS1 | F | 10-19 | IBS | 0.056 | NEGATIVE |
| IBS2 | M | 10-19 | IBS | 0.047 | NEGATIVE |
| IBS3 | M | 5-9 | IBS | 0.099 | NEGATIVE |
| IBS4 | M | 10-19 | IBS | 0.068 | NEGATIVE |
| IBS5 | M | 10-19 | IBS | 0.092 | NEGATIVE |
| IBS6 | F | 20-29 | IBS | 0.121 | NEGATIVE |
| IBS7 | F | 30-39 | IBS | 0.064 | NEGATIVE |

TABLE 39

Clinical and ELISA results for healthy persons.

| Subject ID | Sex | Age Range | ANCA-CHEK OD$_{450}$ | ANCA-CHEK Results |
|---|---|---|---|---|
| D1 | F | 40-49 | 0.087 | NEGATIVE |
| D2 | M | 20-29 | 0.078 | NEGATIVE |
| D5 | M | 20-29 | 0.178 | POSITIVE |
| D15 | M | 50-59 | 0.041 | NEGATIVE |
| D17 | M | 50-59 | 0.039 | NEGATIVE |
| D18 | F | 40-49 | 0.069 | NEGATIVE |
| D19 | F | 60-69 | 0.050 | NEGATIVE |
| D20 | M | 70-79 | 0.039 | NEGATIVE |
| D21 | F | 70-79 | 0.104 | NEGATIVE |
| D22 | M | 60-69 | 0.045 | NEGATIVE |
| D24 | F | 50-59 | 0.054 | NEGATIVE |

In summary, the present invention is directed to a method for the differentiation of inflammatory bowel disease (IBD) from irritable bowel disease (IBS) followed by distinguishing ulcerative colitis and Crohn's disease from other gastrointestinal illnesses. This highly differential method first uses the presence of elevated fecal lactoferrin as a marker of intestinal inflammation to differentiate IBD from IBS. Patients suspected of IBD are then analyzed for fecal anti-*Saccharomyces cerevisiae* antibodies (ASCA) as an indicator of Crohn's disease and fecal anti-neutrophil cytoplasmic antibodies (ANCA) as an indicator of ulcerative colitis. IBD patients are further monitored for intestinal inflammation using fecal lactoferrin to evaluate the effectiveness of medical therapy and predict relapse. The apparatus consists of either a qualitative enzyme-linked immunoassay or other immunoassay that utilizes antibodies specific to total endogenous lactoferrin, ASCA and ANCA in human feces.

The method and apparatus may be used by healthcare providers to identify IBD and distinguish ulcerative colitis and Crohn's disease from other gastrointestinal illnesses. The present invention has been described in relation to particular embodiments, which are intended in all respects to be illustrative rather than restrictive. Alternative embodiments will become apparent to those skilled in the art to which the present invention pertains without departing from its scope.

From the foregoing, it will be seen that this invention is one well adapted to attain all the ends and objects hereinabove set forth together with other advantages which are obvious and which are inherent to the method.

It will be understood that certain features and subcombinations are of utility and may be employed without reference to other features and subcombinations. This is contemplated by and is within the scope of the claims.

The invention claimed is:

1. A method for testing fecal samples from persons for diagnosis, the method comprising:
    obtaining a fecal sample from a person presenting with symptoms common to inflammatory bowel disease and irritable bowel syndrome;
    diluting the sample;
    determining that the sample contains an elevated level of lactoferrin compared to a lactoferrin level in a healthy control;
    measuring the sample for an elevated level of anti-*Saccharomyces cerevisiae* antibodies (ASCA);
    measuring the sample for an elevated level of anti-neutrophil cytoplasmic antibodies (ANCA);
    upon determining that the sample contains an elevated level of anti-*Saccharomyces cerevisiae* antibodies compared to an anti-*Saccharomyces cerevisiae* antibody level in a healthy control and not an elevated level of anti-neutrophil cytoplasmic antibodies, diagnosing the person with Crohn's disease; and
    upon determining that the sample contains an elevated level of anti-neutrophil cytoplasmic antibodies compared to an anti-neutrophil cytoplasmic antibody level in a healthy control and not an elevated level of anti-*Saccharomyces cerevisiae* antibodies, diagnosing the person with ulcerative colitis.

2. The method of claim 1, wherein a diagnosis of inflammatory bowel disease may be concluded based upon the sample containing an elevated level of lactoferrin.

3. The method of claim 1, wherein the lactoferrin, anti-*Saccharomyces cerevisiae* antibodies and anti-neutrophil cytoplasmic antibodies are measured using one of enzyme-linked immunoassays, lateral flow membrane tests and immunoassays utilizing antibodies.

4. The method of claim 1, wherein determining that the sample contains an elevated level of lactoferrin is based on a qualitative ELISA.

5. The method of claim 1, wherein determining that the sample contains an elevated level of lactoferrin is based on a quantitative measurement.

6. The method of claim 1, further comprising:
    contacting the sample with immobilized polyclonal antibodies to endogenous lactoferrin to create a treated sample;
    contacting said treated sample with enzyme-linked polyclonal antibodies such that the enzyme-linked polyclonal antibodies are allowed to bind to captured endogenous lactoferrin creating an enzyme-linked antibody bound sample;
    adding a substrate to the enzyme-linked antibody bound sample to create a readable sample; and
    determining the optical density of said readable sample at 450 nm.

7. The method of claim 1, further comprising:
    contacting the sample with antigens of *Saccharomyces cerevisiae* to create a treated sample;
    contacting the treated sample with polyvalent antibodies to human immunoglobulin conjugated to an enzyme such that the polyvalent antibodies are allowed to bind to capture anti-*Saccharomyces cerevisiae* antibodies creating an enzyme-linked antibody bound sample;
    adding a substrate to the enzyme-linked antibody bound sample to create a readable sample; and
    determining the optical density of the readable sample.

8. The method of claim 1, further comprising:
    contacting the sample with neutrophil cytoplasmic antigens to create a treated sample;
    contacting the treated sample with polyvalent antibodies to human immunoglobulin such that the enzyme-linked polyvalent antibodies are allowed to bind to capture anti-neutrophil cytoplasmic antibodies creating an enzyme-linked antibody bound sample;
    adding an enzyme substrate to the enzyme-linked antibody bound sample to create a readable sample; and
    determining an optical density of the readable sample at 450 nm.

9. A method for testing fecal samples from persons for diagnosis, the method comprising:
    obtaining a fecal sample from a person presenting with symptoms common to inflammatory bowel disease and irritable bowel syndrome;
    diluting the sample;
    contacting the diluted sample with immobilized polyclonal antibodies to endogenous lactoferrin to create a first treated sample;
    contacting said first treated sample with enzyme-linked polyclonal antibodies such that the enzyme-linked polyclonal antibodies are allowed to bind to captured endogenous lactoferrin creating an enzyme-linked antibody bound sample;
    adding a substrate to the enzyme-linked antibody bound sample to create a readable sample;
    determining the optical density of said readable sample at 450 nm;
    determining that the sample contains an elevated level of lactoferrin compared to a lactoferrin level in a healthy control;
    measuring the sample for an elevated level of anti-*Saccharomyces cerevisiae* antibodies (ASCA);
    measuring the sample for an elevated level of anti-neutrophil cytoplasmic antibodies (ANCA);
    upon determining that the sample contains an elevated level of anti-*Saccharomyces cerevisiae* antibodies compared to an anti-*Saccharomyces cerevisiae* antibody level in a healthy control and not an elevated level of anti-neutrophil cytoplasmic antibodies, diagnosing the person with Crohn's disease; and upon determining that the sample contains an elevated level of anti-neutrophil cytoplasmic antibodies compared to an anti-neutrophil cytoplasmic antibody level in a healthy control and not an elevated level of anti-*Saccharomyces cerevisiae* antibodies, diagnosing the person with ulcerative colitis.

10. The method of claim 9, further comprising:

contacting the sample with antigens of *Saccharomyces cerevisiae* to create a second treated sample;

contacting the second treated sample with polyvalent antibodies to human immunoglobulin conjugated to an enzyme such that the polyvalent antibodies are allowed to bind to capture anti-*Saccharomyces cerevisiae* antibodies creating an enzyme-linked antibody bound sample;

adding a substrate to the enzyme-linked antibody bound sample to create a readable sample; and determining the optical density of the readable sample.

11. A method for testing fecal samples from persons for diagnosis, the method comprising:

obtaining a fecal sample from a person presenting with symptoms common to inflammatory bowel disease and irritable bowel syndrome;

diluting the sample;

contacting the sample with neutrophil cytoplasmic antigens to create a treated sample;

contacting the treated sample with polyvalent antibodies to human immunoglobulin such that the enzyme-linked polyvalent antibodies are allowed to bind to capture anti-neutrophil cytoplasmic antibodies creating an enzyme-linked antibody bound sample;

adding an enzyme substrate to the enzyme-linked antibody bound sample to create a readable sample;

determining an optical density of the readable sample at 450 nm;

determining that the sample contains an elevated level of lactoferrin compared to a lactoferrin level in a healthy control;

measuring the sample for an elevated level of anti-*Saccharomyces cerevisiae* antibodies (ASCA);

measuring the sample for an elevated level of anti-neutrophil cytoplasmic antibodies (ANCA);

upon determining that the sample contains an elevated level of anti-*Saccharomyces cerevisiae* antibodies compared to an anti-*Saccharomyces cerevisiae* antibody level in a healthy control and not an elevated level of anti-neutrophil cytoplasmic antibodies, diagnosing the person with Crohn's disease; and upon determining that the sample contains an elevated level of anti-neutrophil cytoplasmic antibodies compared to an anti-neutrophil antibody level in a healthy control and not an elevated level of anti-*Saccharomyces cerevisiae* antibodies, diagnosing the person with ulcerative colitis.

* * * * *